US012702479B2

(12) United States Patent
Massimini et al.

(10) Patent No.: US 12,702,479 B2
(45) Date of Patent: Aug. 11, 2026

(54) LASER PULSE SHAPING TO ENHANCE CONVERSION EFFICIENCY AND PROTECT FIBER OPTIC DELIVERY SYSTEM FOR DISRUPTION OF VASCULAR CALCIUM

(71) Applicant: Boston Scientific Scimed, Inc., Maple Grove, MN (US)

(72) Inventors: Daniel Massimini, Brooklyn Park, MN (US); Roger McGowan, Otsego, MN (US); Haiping Shao, Plymouth, MN (US); Christopher A. Cook, Laguna Niguel, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1101 days.

(21) Appl. No.: 17/190,921

(22) Filed: Mar. 3, 2021

(65) Prior Publication Data

US 2021/0275249 A1 Sep. 9, 2021

Related U.S. Application Data

(60) Provisional application No. 62/987,060, filed on Mar. 9, 2020.

(51) Int. Cl.
*A61B 18/26* (2006.01)
*A61B 17/00* (2006.01)
(Continued)

(52) U.S. Cl.
CPC .... *A61B 18/26* (2013.01); *A61B 2017/00159* (2013.01); *A61B 2017/00185* (2013.01);
(Continued)

(58) Field of Classification Search
CPC ...................................................... A61B 18/26
See application file for complete search history.

(56) References Cited

U.S. PATENT DOCUMENTS 4,649,924 A 3/1987 Taccardi
4,699,147 A 10/1987 Chilson et al.
(Continued)

FOREIGN PATENT DOCUMENTS

AU 2017205323 1/2022
AU 2019452180 1/2022
(Continued)

OTHER PUBLICATIONS

International Search Report and Written Opinion dated Nov. 8, 2022 in PCT Application Serial No. PCTUS/2022/039678.
(Continued)

*Primary Examiner* — Benjamin J Klein
*Assistant Examiner* — Thien Jason Tran
(74) *Attorney, Agent, or Firm* — SEAGER, TUFTE & WICKHEM, LLP

(57) ABSTRACT

A catheter system includes a power source, a controller, and a light guide. The power source generates a plurality of energy pulses. The controller controls the power source so that the plurality of energy pulses cooperate to produce a composite energy pulse having a composite pulse shape. The light guide receives the composite energy pulse. The light guide emits light energy in a direction away from the light guide to generate a plasma pulse away from the light guide. The power source can be a laser and the light guide can be an optical fiber. Each of the energy pulses has a pulse width, and the energy pulses are added to one another so that the composite energy pulse has a pulse width that is longer than the pulse width of any one of the energy pulses. At least two of the energy pulses can have the same wavelength as or a different wavelength from one another.

20 Claims, 6 Drawing Sheets

(51) Int. Cl.
*A61B 18/00* (2006.01)
*A61B 18/22* (2006.01)
(52) U.S. Cl.
CPC ................ *A61B 2018/0022* (2013.01); *A61B 2018/00369* (2013.01); *A61B 2018/00404* (2013.01); *A61B 2018/00702* (2013.01); *A61B 2018/00761* (2013.01); *A61B 2018/266* (2013.01)

(56) References Cited

U.S. PATENT DOCUMENTS 4,799,479 A 1/1989 Spears
4,850,351 A 7/1989 Herman
4,913,142 A 4/1990 Kittrell et al.
4,932,954 A 6/1990 Wondrazek et al.
4,955,895 A 9/1990 Suglyama
4,960,108 A 10/1990 Reichel et al.
4,994,059 A 2/1991 Kosa et al.
4,998,930 A 3/1991 Lundahl
5,009,658 A * 4/1991 Damgaard-Iversen ..................... H01S 3/109 606/2.5
5,019,075 A 5/1991 Spears et al.
5,034,010 A 7/1991 Kittrell et al.
5,041,121 A 8/1991 Wondrazek et al.
5,057,106 A 10/1991 Kasevich et al.
5,082,343 A 1/1992 Coult et al.
5,093,877 A 3/1992 Aita et al.
5,104,391 A 4/1992 Ingle
5,104,392 A 4/1992 Kittrell et al.
5,109,452 A 4/1992 Selvin et al.
5,116,227 A 5/1992 Levy
5,126,165 A 6/1992 Akihama et al.
5,152,768 A 10/1992 Bhatta
5,173,049 A 12/1992 Levy
5,176,674 A 1/1993 Hofmann
5,181,921 A 1/1993 Makita et al.
5,188,632 A 2/1993 Goldenberg
5,200,838 A 4/1993 Nudelman
5,269,777 A 12/1993 Doiron
5,290,277 A 3/1994 Vercimak et al.
5,321,715 A 6/1994 Trost
5,324,282 A 6/1994 Dodick
5,328,472 A 7/1994 Steinke et al.
5,330,517 A 7/1994 Mordon et al.
5,336,184 A 8/1994 Teirstein
5,363,458 A 11/1994 Pan
5,372,138 A 12/1994 Crowley
5,387,225 A 2/1995 Euteneur
5,400,428 A 3/1995 Grace
5,410,797 A 5/1995 Steinke et al.
5,417,689 A 5/1995 Fine
5,422,926 A 6/1995 Smith
5,431,647 A 7/1995 Purcell
5,454,809 A 10/1995 Janssen
5,456,680 A 10/1995 Taylor
5,474,537 A 12/1995 Solar
5,496,311 A 3/1996 Abele et al.
5,509,917 A 4/1996 Cecchetti
5,519,798 A 5/1996 Shahid
5,540,679 A 7/1996 Fram
5,562,657 A 10/1996 Griffin
5,598,494 A 1/1997 Behrmann et al.
5,609,606 A 3/1997 O'Boyle
5,611,807 A 3/1997 O'Boyle
5,632,739 A 5/1997 Anderson et al.
5,637,877 A 6/1997 Sinofsky
5,661,829 A 8/1997 Zheng
5,697,377 A 12/1997 Wittkamph
5,718,241 A 2/1998 Ben-Haim et al.
5,729,583 A 3/1998 Tang
5,764,843 A 6/1998 Macken et al.
5,772,609 A 6/1998 Nguyen et al.
5,860,974 A 1/1999 Abele
5,891,135 A 4/1999 Jackson et al.
5,906,611 A 5/1999 Dodick et al.
5,944,697 A 8/1999 Benett et al.
6,007,514 A 12/1999 Nita
6,015,404 A 1/2000 Altshuler
6,080,119 A 6/2000 Schwarze et al.
6,123,923 A 9/2000 Unger
6,139,510 A 10/2000 Palermo
6,186,963 B1 2/2001 Schwarze et al.
6,203,537 B1 * 3/2001 Adrian .................. A61B 18/26 606/1
6,210,404 B1 4/2001 Shadduck
6,339,470 B1 1/2002 Papademetriou et al.
6,356,575 B1 3/2002 Fukumoto
6,368,318 B1 4/2002 Visuri et al.
6,500,174 B1 12/2002 Maguire et al.
6,514,203 B2 2/2003 Bukshpan
6,514,249 B1 2/2003 Maguire
6,524,251 B2 2/2003 Rabiner et al.
6,538,739 B1 3/2003 Visuri et al.
6,544,218 B1 4/2003 Choi
6,548,010 B1 4/2003 Stivland et al.
6,560,387 B1 5/2003 Hehlen et al.
6,607,502 B1 8/2003 Maguire et al.
6,631,220 B1 10/2003 Liang et al.
6,652,547 B2 11/2003 Rabiner et al.
6,666,834 B2 12/2003 Restle et al.
6,702,781 B1 3/2004 Reifart et al.
6,773,447 B2 8/2004 Laguna
6,824,554 B1 11/2004 Jang
6,849,994 B1 2/2005 White et al.
6,890,317 B2 5/2005 Gerdts et al.
6,947,785 B1 9/2005 Beatty et al.
6,966,890 B2 11/2005 Coyle et al.
6,978,168 B2 12/2005 Beatty et al.
6,990,370 B1 1/2006 Beatty et al.
7,273,470 B2 9/2007 Wantink
7,309,324 B2 12/2007 Hayes et al.
7,367,967 B2 5/2008 Eidenschink
7,470,240 B2 12/2008 Schultheiss et al.
7,539,231 B1 5/2009 Honea et al.
7,569,032 B2 8/2009 Naimark et al.
7,599,588 B2 10/2009 Eberle et al.
7,641,646 B2 1/2010 Kennedy, II
7,691,079 B2 4/2010 Gobel
7,713,260 B2 5/2010 Lessard
7,758,572 B2 7/2010 Weber et al.
7,762,984 B2 7/2010 Kumoyama et al.
7,810,395 B2 10/2010 Zhou
7,850,685 B2 12/2010 Kunis et al.
7,867,178 B2 1/2011 Simnacher
7,909,797 B2 3/2011 Kennedy, II et al.
7,942,850 B2 5/2011 Levit et al.
7,967,781 B2 6/2011 Simpson et al.
7,972,299 B2 7/2011 Carter
7,985,189 B1 7/2011 Ogden et al.
8,021,328 B2 9/2011 Lee
8,029,473 B2 10/2011 Carter
8,043,256 B2 10/2011 Hansen
8,066,732 B2 11/2011 Paul et al.
8,088,121 B2 1/2012 Nishide
8,157,760 B2 4/2012 Criado et al.
8,162,859 B2 4/2012 Schultheiss et al.
8,166,825 B2 5/2012 Zhou
8,192,368 B2 6/2012 Woodruff
8,197,505 B2 6/2012 Hirszowicz et al.
8,246,643 B2 8/2012 Nita
8,267,886 B2 9/2012 Ewing
8,292,913 B2 10/2012 Warnack
8,328,820 B2 12/2012 Diamant
8,364,235 B2 1/2013 Kordis et al.
8,372,034 B2 2/2013 Levit
8,382,738 B2 2/2013 Simpson et al.
8,414,527 B2 4/2013 Mallaby
8,419,613 B2 4/2013 Saadat
8,439,890 B2 5/2013 Beyar
8,556,813 B2 10/2013 Cashman et al.
8,556,851 B2 10/2013 Hirszowicz
8,574,247 B2 11/2013 Adams et al.

(56) References Cited

U.S. PATENT DOCUMENTS 8,657,814 B2 2/2014 Werneth
8,709,075 B2 4/2014 Adams et al.
8,728,091 B2 5/2014 Hakala et al.
8,734,424 B2 5/2014 Watanabe
8,747,416 B2 6/2014 Hakala et al.
8,784,362 B2 7/2014 Boutilette
8,834,510 B2 9/2014 Wilson et al.
8,888,788 B2 11/2014 Hakala et al.
8,956,371 B2 2/2015 Hawkins et al.
8,956,374 B2 2/2015 Hawkins et al.
8,986,339 B2 3/2015 Warnack
8,992,519 B2 3/2015 Kim et al.
8,992,817 B2 3/2015 Stamberg
9,005,216 B2 4/2015 Hakala et al.
9,011,462 B2 4/2015 Adams et al.
9,011,463 B2 4/2015 Adams et al.
9,011,511 B2 4/2015 Gregorich
9,044,575 B2 6/2015 Beasley et al.
9,044,618 B2 6/2015 Hawkins et al.
9,044,619 B2 6/2015 Hawkins et al.
9,056,185 B2 6/2015 Fischell et al.
9,072,534 B2 7/2015 Adams et al.
9,089,669 B2 7/2015 Haslinger et al.
9,131,949 B2 9/2015 Coleman et al.
9,138,249 B2 9/2015 Adams et al.
9,138,260 B2 9/2015 Miller et al.
9,180,280 B2 11/2015 Hawkins et al.
9,220,521 B2 12/2015 Hawkins et al.
9,237,984 B2 1/2016 Hawkins et al.
9,254,169 B2 2/2016 Long et al.
9,282,984 B2 3/2016 Nita
9,283,359 B2 3/2016 Pepper
9,289,132 B2 3/2016 Ghaffari et al.
9,289,224 B2 3/2016 Adams et al.
9,289,319 B2 3/2016 Pacetti et al.
9,320,530 B2 4/2016 Grace
9,333,000 B2 5/2016 Hakala et al.
9,339,632 B2 5/2016 Eidenschink et al.
9,364,645 B2 6/2016 Erikawa
9,375,223 B2 6/2016 Wallace
9,421,025 B2 8/2016 Hawkins et al.
9,433,428 B2 9/2016 Hakala et al.
9,433,745 B2 9/2016 Cully
9,504,809 B2 11/2016 Bo
9,510,887 B2 12/2016 Burnett
9,522,012 B2 12/2016 Adams
9,554,815 B2 1/2017 Adams et al.
9,555,267 B2 1/2017 Ein-Gal
9,566,209 B2 2/2017 Katragadda et al.
9,579,114 B2 2/2017 Mantell et al.
9,579,492 B2 2/2017 Simpson
9,585,684 B2 3/2017 Nita et al.
9,592,328 B2 3/2017 Jeevanandam
9,603,506 B2 3/2017 Goldfarb et al.
9,629,567 B2 4/2017 Porath et al.
9,642,673 B2 5/2017 Adams
9,662,069 B2 5/2017 De Graff et al.
9,687,166 B2 6/2017 Subramaniam
9,700,655 B2 7/2017 Laudenslager et al.
9,730,715 B2 8/2017 Adams
9,737,361 B2 8/2017 Magana
9,764,142 B2 9/2017 Imran
9,782,570 B2 10/2017 Hirszowicz
9,814,476 B2 11/2017 Adams et al.
9,833,348 B2 12/2017 Jordan et al.
9,839,764 B2 12/2017 Chouinard
9,861,377 B2 1/2018 Mantell et al.
9,867,629 B2 1/2018 Hawkins et al.
9,878,135 B2 1/2018 Holzapfel et al.
9,894,756 B2 2/2018 Weinkam et al.
9,901,704 B2 2/2018 Appling
9,955,946 B2 5/2018 Miller et al.
9,974,963 B2 5/2018 Imran
9,974,970 B2 5/2018 Nuta et al.
9,993,292 B2 6/2018 Adams et al.
10,039,561 B2 8/2018 Adams et al.
10,076,384 B2 9/2018 Kasprzyk
10,086,175 B2 10/2018 Torres et al.
10,124,153 B2 11/2018 Feig
10,136,829 B2 11/2018 Deno et al.
10,149,690 B2 12/2018 Hawkins et al.
10,159,505 B2 12/2018 Hakala et al.
10,194,994 B2 2/2019 Deno et al.
10,201,387 B2 2/2019 Grace et al.
10,206,698 B2 2/2019 Hakala et al.
10,226,265 B2 3/2019 Ku et al.
10,245,410 B2 4/2019 Aggerholm
10,327,846 B1 6/2019 Stark et al.
10,328,290 B2 6/2019 Zhou et al.
10,357,264 B2 7/2019 Kat-Kuoy
10,405,923 B2 9/2019 Yu et al.
10,406,031 B2 9/2019 Thyzel
10,406,318 B2 9/2019 Williams
10,420,569 B2 9/2019 Adams
10,439,791 B2 10/2019 Kalhan
10,441,300 B2 10/2019 Hawkins
10,449,339 B2 10/2019 Wilson et al.
10,463,430 B2 11/2019 Dick
10,478,202 B2 11/2019 Adams et al.
10,517,620 B2 12/2019 Adams
10,517,621 B1 12/2019 Hakala et al.
10,537,287 B2 1/2020 Braido et al.
10,555,744 B2 2/2020 Nguyen et al.
10,561,428 B2 2/2020 Eggert et al.
10,583,277 B2 3/2020 Rundquist
10,589,073 B2 3/2020 Mallaby
10,617,850 B2 4/2020 Tal
10,646,240 B2 5/2020 Betelia et al.
10,668,245 B2 6/2020 Kanae
10,682,178 B2 6/2020 Adams et al.
10,695,531 B2 6/2020 Suzuki
10,702,293 B2 7/2020 Adams et al.
10,709,462 B2 7/2020 Nguyen et al.
10,709,872 B2 7/2020 Alvarez et al.
10,758,255 B2 9/2020 Adams
10,797,684 B1 10/2020 Benz et al.
10,799,688 B2 10/2020 Calhoun
10,842,567 B2 11/2020 Grace et al.
10,850,075 B2 12/2020 Tarunaga
10,857,329 B2 12/2020 Davies
10,933,225 B2 3/2021 Campbell
10,952,740 B2 3/2021 Dasnurkar et al.
10,952,790 B2 3/2021 Haverkost et al.
10,959,743 B2 3/2021 Adams et al.
10,966,737 B2 4/2021 Nguyen
10,967,156 B2 4/2021 Gulachenski
10,973,538 B2 4/2021 Hakala et al.
10,974,028 B2 4/2021 Buller et al.
10,980,987 B2 4/2021 Tarunaga
11,000,299 B2 5/2021 Hawkins et al.
11,020,135 B1 6/2021 Hawkins
11,026,707 B2 6/2021 Ku et al.
11,040,176 B2 6/2021 Blanchard et al.
11,058,492 B2 7/2021 Grace et al.
11,076,874 B2 8/2021 Hakala et al.
11,116,939 B2 9/2021 Jamous et al.
11,141,131 B2 10/2021 Stigall
11,179,169 B2 11/2021 Brouillete et al.
11,207,493 B2 12/2021 Suzuki et al.
11,213,661 B2 1/2022 Spindler
11,229,772 B2 1/2022 Nita
11,229,776 B2 1/2022 Kugler et al.
11,246,659 B2 2/2022 Grace et al.
11,253,681 B2 2/2022 Williams
11,266,817 B2 3/2022 Cope et al.
11,389,171 B2 7/2022 Goldsmith
11,389,628 B2 7/2022 Spencer
11,395,669 B2 7/2022 O'Malley et al.
11,399,862 B2 8/2022 Massimini et al.
11,406,452 B2 8/2022 Efremkin
11,406,799 B2 8/2022 McEvaddy et al.
11,484,327 B2 11/2022 Anderson et al.
11,540,848 B2 1/2023 Cai et al.
11,564,729 B2 1/2023 Walzman

(56) References Cited

U.S. PATENT DOCUMENTS 11,602,363 B2 3/2023 Nguyen
11,633,200 B2 4/2023 Anderson et al.
11,672,585 B2 6/2023 Schultheis
11,672,599 B2 6/2023 Schultheis et al.
11,707,323 B2 7/2023 Schultheis et al.
11,771,449 B2 10/2023 Adams et al.
11,779,363 B2 10/2023 Vo
11,826,530 B2 11/2023 Suzuki
11,839,391 B2 12/2023 Schultheis et al.
11,911,054 B2 2/2024 Singla
11,950,793 B2 4/2024 Nguyen
12,011,185 B2 6/2024 Vo
12,023,098 B2 7/2024 Nguyen
12,035,932 B1 7/2024 Nunes
12,076,077 B2 9/2024 Mori
12,144,516 B2 11/2024 Betelia
12,178,458 B1 12/2024 Betelia et al.
12,193,691 B2 1/2025 Adams
2001/0016761 A1 8/2001 Rudie
2001/0018569 A1 8/2001 Erbel
2001/0020164 A1 9/2001 Papademetriou
2001/0049464 A1 12/2001 Ganz
2001/0051784 A1 12/2001 Brisken
2002/0045811 A1 4/2002 Kittrell et al.
2002/0052621 A1 5/2002 Fried et al.
2002/0065512 A1 5/2002 Fjield et al.
2002/0082553 A1 6/2002 Duchamp
2002/0183620 A1 12/2002 Tearney
2002/0183729 A1 12/2002 Farr et al.
2002/0188204 A1 12/2002 McNamara et al.
2003/0009157 A1 1/2003 Levine et al.
2003/0050632 A1 3/2003 Fjield et al.
2003/0065316 A1 4/2003 Levine et al.
2003/0114901 A1 6/2003 Loeb et al.
2003/0125719 A1 7/2003 Furnish
2003/0144654 A1 7/2003 Hilal
2003/0176873 A1 9/2003 Chernenko et al.
2004/0002677 A1 1/2004 Gentsler
2004/0024349 A1 2/2004 Flock et al.
2004/0073251 A1 4/2004 Weber
2004/0097996 A1 5/2004 Rabiner
2004/0133254 A1 7/2004 Sterzer et al.
2004/0162508 A1 8/2004 Uebelacker
2004/0210278 A1 10/2004 Boll
2004/0243119 A1 12/2004 Lane et al.
2004/0249401 A1 12/2004 Rabiner
2004/0254570 A1 12/2004 Hadsjicostis
2005/0010095 A1 1/2005 Stewart et al.
2005/0021013 A1 1/2005 Visuri
2005/0080396 A1 4/2005 Rontal
2005/0113722 A1 5/2005 Schultheiss
2005/0171437 A1 8/2005 Carberry
2005/0171527 A1 8/2005 Bhola
2005/0251131 A1 11/2005 Lesh
2005/0259319 A1 11/2005 Brooker
2005/0273014 A1 12/2005 Gianchandani et al.
2005/0277839 A1 12/2005 Alderman et al.
2006/0033241 A1 2/2006 Schewe et al.
2006/0084966 A1 4/2006 Maguire et al.
2006/0098921 A1 5/2006 Benaron et al.
2006/0142703 A1 6/2006 Carter
2006/0190022 A1 8/2006 Beyar et al.
2006/0200039 A1 9/2006 Brockway et al.
2006/0221528 A1 10/2006 Li et al.
2006/0241524 A1 10/2006 Lee et al.
2006/0241572 A1 10/2006 Zhou
2006/0241733 A1 10/2006 Zhang et al.
2006/0270976 A1 11/2006 Savage et al.
2007/0027524 A1 2/2007 Johnson
2007/0043340 A1 2/2007 Thyzel
2007/0060990 A1 3/2007 Satake
2007/0088380 A1 4/2007 Hirszowicz et al.
2007/0118057 A1 5/2007 Ein-gal
2007/0142779 A1 6/2007 Duane
2007/0142819 A1 6/2007 El-Nounou et al.
2007/0142821 A1 6/2007 Hennessy et al.
2007/0142856 A1 6/2007 Jang
2007/0179496 A1 8/2007 Swoyer
2007/0239082 A1 10/2007 Schultheiss et al.
2007/0255270 A1 11/2007 Carney
2007/0264353 A1 11/2007 Myntti et al.
2007/0270897 A1 11/2007 Skerven
2007/0280311 A1 12/2007 Hofmann
2007/0299392 A1 12/2007 Beyar et al.
2008/0033519 A1 2/2008 Burwell
2008/0081950 A1 4/2008 Koenig et al.
2008/0086118 A1 4/2008 Lai
2008/0095714 A1 4/2008 Castella et al.
2008/0097251 A1 4/2008 Babaev
2008/0108867 A1 5/2008 Zhou
2008/0114341 A1 5/2008 Thyzel
2008/0132810 A1 6/2008 Scoseria et al.
2008/0175539 A1 7/2008 Brown
2008/0195088 A1 8/2008 Farr et al.
2008/0214891 A1 9/2008 Slenker et al.
2008/0281157 A1 11/2008 Miyagi et al.
2008/0296152 A1 12/2008 Voss
2008/0319356 A1 12/2008 Cain et al.
2009/0036803 A1 2/2009 Warlick et al.
2009/0043300 A1 2/2009 Reitmajer et al.
2009/0054881 A1 2/2009 Krespi
2009/0097806 A1 4/2009 Viellerobe et al.
2009/0125007 A1 5/2009 Splinter
2009/0131921 A1 5/2009 Kurtz et al.
2009/0192495 A1 7/2009 Ostrovsky et al.
2009/0240242 A1 9/2009 Neuberger
2009/0247945 A1 10/2009 Levit
2009/0281531 A1 11/2009 Rizoiu
2009/0292296 A1 11/2009 Pansky
2009/0296751 A1 12/2009 Kewitsch et al.
2009/0299327 A1 12/2009 Tilson et al.
2009/0306533 A1 12/2009 Rousche
2009/0312768 A1 12/2009 Hawkins et al.
2010/0016862 A1 1/2010 Hawkins et al.
2010/0036238 A1 2/2010 Neidert
2010/0036294 A1 2/2010 Mantell et al.
2010/0063491 A1 3/2010 Verhagen
2010/0094209 A1 4/2010 Drasler et al.
2010/0114020 A1 5/2010 Hawkins et al.
2010/0114065 A1 5/2010 Hawkins et al.
2010/0125268 A1 5/2010 Gustus et al.
2010/0160838 A1 6/2010 Krespi
2010/0160903 A1 6/2010 Krespi
2010/0168572 A1 7/2010 Sliwa
2010/0168836 A1 7/2010 Kassab
2010/0168862 A1 7/2010 Edie et al.
2010/0179632 A1 7/2010 Bruszewski et al.
2010/0191089 A1 7/2010 Stebler et al.
2010/0198114 A1 8/2010 Novak et al.
2010/0199773 A1 8/2010 Zhou
2010/0222786 A1 9/2010 Kassab
2010/0234875 A1 9/2010 Allex et al.
2010/0256535 A1 10/2010 Novak et al.
2010/0265733 A1 10/2010 O'Leary
2010/0286791 A1 11/2010 Goldsmith
2010/0316333 A1 12/2010 Luther
2011/0034832 A1* 2/2011 Cioanta ............ A61B 17/22029 601/1
2011/0059415 A1 3/2011 Kasenbacher
2011/0082452 A1 4/2011 Melsky
2011/0082534 A1 4/2011 Wallace
2011/0118634 A1 5/2011 Golan
2011/0144502 A1 6/2011 Zhou et al.
2011/0184244 A1 7/2011 Kagaya et al.
2011/0208185 A1 8/2011 Diamant et al.
2011/0213349 A1 9/2011 Brown
2011/0245740 A1 10/2011 Novak et al.
2011/0257641 A1 10/2011 Hastings et al.
2011/0263921 A1 10/2011 Vrba et al.
2011/0275990 A1 11/2011 Besser et al.
2011/0306956 A1 12/2011 Islam
2012/0064141 A1 3/2012 Andreacchi et al.
2012/0071715 A1 3/2012 Beyar et al.
2012/0071867 A1 3/2012 Ryan

(56) References Cited

U.S. PATENT DOCUMENTS

2012/0071889 A1 3/2012 Mantell et al.
2012/0089132 A1 4/2012 Dick et al.
2012/0095335 A1 4/2012 Sverdlik et al.
2012/0095461 A1 4/2012 Herscher et al.
2012/0116289 A1 5/2012 Hawkins et al.
2012/0116486 A1 5/2012 Naga et al.
2012/0123331 A1 5/2012 Satake
2012/0123399 A1 5/2012 Belikov
2012/0143131 A1 6/2012 Tun
2012/0157892 A1 6/2012 Reitmajer et al.
2012/0197245 A1 8/2012 Burnett
2012/0203255 A1 8/2012 Hawkins et al.
2012/0221013 A1 8/2012 Hawkins et al.
2012/0232409 A1 9/2012 Stahmann
2012/0296367 A1 11/2012 Grovender et al.
2012/0323211 A1 12/2012 Ogle
2012/0330293 A1 12/2012 Arai
2013/0030431 A1 1/2013 Adams
2013/0030447 A1 1/2013 Adams
2013/0041355 A1 2/2013 Heeren et al.
2013/0046207 A1 2/2013 Capelli
2013/0046293 A1 2/2013 Arai et al.
2013/0053762 A1 2/2013 Rontal et al.
2013/0060234 A1 3/2013 Besser
2013/0110003 A1 5/2013 Surti
2013/0116714 A1 5/2013 Adams et al.
2013/0190803 A1 7/2013 Angel et al.
2013/0197614 A1 8/2013 Gustus
2013/0218054 A1 8/2013 Sverdlik et al.
2013/0226131 A1 8/2013 Bacino et al.
2013/0253466 A1 9/2013 Campbell
2013/0274726 A1 10/2013 Takayama
2013/0310819 A1 11/2013 Neuberger et al.
2013/0345617 A1 12/2013 Wallace
2014/0005576 A1 1/2014 Adams
2014/0005706 A1 1/2014 Gelfand et al.
2014/0012186 A1 1/2014 Thyzel
2014/0039002 A1 2/2014 Diodone et al.
2014/0039358 A1 2/2014 Zhou et al.
2014/0039513 A1 2/2014 Hakala
2014/0046229 A1 2/2014 Hawkins et al.
2014/0046353 A1 2/2014 Adams
2014/0052146 A1 2/2014 Curtis et al.
2014/0052147 A1 2/2014 Hakala et al.
2014/0058294 A1 2/2014 Gross et al.
2014/0074111 A1 3/2014 Hakala
2014/0114198 A1 4/2014 Samada et al.
2014/0128848 A1 5/2014 Appling et al.
2014/0153087 A1 6/2014 Hutchings et al.
2014/0155990 A1 6/2014 Nyuli
2014/0180069 A1 6/2014 Millett
2014/0180126 A1 6/2014 Millett
2014/0180134 A1 6/2014 Hoseit
2014/0188094 A1 7/2014 Islam
2014/0228829 A1 8/2014 Schmitt
2014/0257144 A1 9/2014 Capelli et al.
2014/0257148 A1 9/2014 Jie
2014/0276573 A1 9/2014 Miesel
2014/0288570 A1 9/2014 Adams
2014/0309536 A1 10/2014 Douk et al.
2014/0336626 A1 11/2014 Jiang
2014/0336632 A1 11/2014 Toth
2014/0357997 A1 12/2014 Hartmann
2015/0005576 A1 1/2015 Diodone et al.
2015/0039002 A1 2/2015 Hawkins
2015/0057648 A1 2/2015 Swift et al.
2015/0071591 A1 3/2015 Chen
2015/0073430 A1 3/2015 Hakala et al.
2015/0080875 A1 3/2015 Kasprzyk et al.
2015/0100048 A1 4/2015 Hiereth et al.
2015/0105715 A1 4/2015 Pikus et al.
2015/0119870 A1 4/2015 Rudie
2015/0126990 A1 5/2015 Sharma
2015/0141764 A1 5/2015 Harks et al.
2015/0250542 A1 9/2015 Islam
2015/0276689 A1 10/2015 Watanabe
2015/0313732 A1 11/2015 Fulton, III
2015/0320432 A1* 11/2015 Adams ............. A61B 17/22012 606/128
2015/0342678 A1 12/2015 Deladurantaye et al.
2015/0342681 A1 12/2015 Lee
2015/0359432 A1 12/2015 Ehrenreich
2015/0359557 A1 12/2015 Shimokawa
2016/0008016 A1 1/2016 Cioanta et al.
2016/0015471 A1 1/2016 Piron et al.
2016/0016016 A1 1/2016 Taylor et al.
2016/0018602 A1 1/2016 Govari et al.
2016/0022294 A1 1/2016 Cioanta et al.
2016/0038087 A1 2/2016 Hunter
2016/0095610 A1 4/2016 Lipowski et al.
2016/0135828 A1 5/2016 Hawkins et al.
2016/0135891 A1 5/2016 Feldman
2016/0143522 A1 5/2016 Ransbury
2016/0151639 A1 6/2016 Scharf et al.
2016/0183819 A1 6/2016 Burnett
2016/0183957 A1 6/2016 Hakala et al.
2016/0184020 A1 6/2016 Kowalewski et al.
2016/0184022 A1 6/2016 Grace et al.
2016/0184023 A1 6/2016 Grace et al.
2016/0184526 A1 6/2016 Beyar
2016/0184570 A1 6/2016 Grace et al.
2016/0228187 A1 8/2016 Gross
2016/0234534 A1 8/2016 Kitahara et al.
2016/0262784 A1 9/2016 Grace et al.
2016/0270806 A1 9/2016 Wallace
2016/0302762 A1 10/2016 Stigall et al.
2016/0324564 A1 11/2016 Gerlach et al.
2016/0331389 A1 11/2016 Hakala et al.
2016/0339204 A1 11/2016 Williams
2016/0367274 A1 12/2016 Wallace
2016/0367275 A1 12/2016 Wallace
2017/0036253 A1 2/2017 Lukac et al.
2017/0049463 A1 2/2017 Popovic et al.
2017/0056035 A1 3/2017 Adams
2017/0056087 A1 3/2017 Buckley
2017/0086867 A1 3/2017 Adams
2017/0119469 A1 5/2017 Shimizu et al.
2017/0119470 A1 5/2017 Diamant et al.
2017/0135709 A1 5/2017 Nguyen et al.
2017/0151421 A1 6/2017 Asher
2017/0209050 A1 7/2017 Fengler et al.
2017/0265942 A1* 9/2017 Grace .................. A61B 18/245
2017/0303946 A1 10/2017 Ku et al.
2017/0311965 A1 11/2017 Adams
2017/0354464 A1 12/2017 Waisman et al.
2018/0008348 A1 1/2018 Grace et al.
2018/0042661 A1 2/2018 Long
2018/0042677 A1 2/2018 Yu et al.
2018/0045897 A1 2/2018 Chia
2018/0049877 A1 2/2018 Venkatasubramanian
2018/0085174 A1 3/2018 Radtke et al.
2018/0092763 A1 4/2018 Dagan et al.
2018/0095287 A1 4/2018 Jeng et al.
2018/0098779 A1 4/2018 Betelia et al.
2018/0152568 A1 5/2018 Thumpudi et al.
2018/0169392 A1 6/2018 Franklin
2018/0238675 A1 8/2018 Wan
2018/0256250 A1 9/2018 Adams et al.
2018/0280005 A1 10/2018 Parmentier
2018/0303501 A1 10/2018 Hawkins
2018/0303503 A1 10/2018 Eggert et al.
2018/0303504 A1 10/2018 Eggert et al.
2018/0304053 A1 10/2018 Eggert et al.
2018/0323571 A1 11/2018 Brown et al.
2018/0333043 A1 11/2018 Teriluc
2018/0360482 A1 12/2018 Nguyen
2019/0029702 A1 1/2019 De Cicco
2019/0029703 A1 1/2019 Wasdyke et al.
2019/0069916 A1 3/2019 Hawkins et al.
2019/0072378 A1 3/2019 Hane et al.
2019/0097380 A1 3/2019 Luft et al.
2019/0099588 A1 4/2019 Ramanath et al.
2019/0104933 A1 4/2019 Stern
2019/0117242 A1* 4/2019 Lawinger ........... A61M 25/1011

(56) References Cited

U.S. PATENT DOCUMENTS

2019/0150960 A1 5/2019 Nguyen et al.
2019/0150961 A1 5/2019 Tozzi
2019/0159792 A1 5/2019 Panian
2019/0167349 A1 6/2019 Shamay
2019/0175111 A1 6/2019 Genereux et al.
2019/0175300 A1 6/2019 Horn et al.
2019/0175372 A1 6/2019 Boyden et al.
2019/0175407 A1 6/2019 Bacher
2019/0209368 A1 7/2019 Park et al.
2019/0232066 A1 8/2019 Lim et al.
2019/0247680 A1 8/2019 Mayer
2019/0262594 A1 8/2019 Ogata et al.
2019/0265419 A1 8/2019 Tayebati
2019/0282249 A1 9/2019 Tran et al.
2019/0282250 A1 9/2019 Tran et al.
2019/0285803 A1 9/2019 Van Zuylen
2019/0321100 A1 10/2019 Masotti et al.
2019/0321101 A1 10/2019 Massoti et al.
2019/0328259 A1 10/2019 Deno et al.
2019/0365400 A1 12/2019 Adams et al.
2019/0380589 A1 12/2019 Lloret
2019/0388002 A1 12/2019 Bozsak et al.
2019/0388110 A1 12/2019 Nguyen et al.
2019/0388133 A1 12/2019 Sharma
2019/0388151 A1 12/2019 Bhawalkar
2019/0388654 A1 12/2019 Chou
2020/0000484 A1 1/2020 Hawkins
2020/0008856 A1 1/2020 Harmouche
2020/0022754 A1 1/2020 Cottone
2020/0038087 A1 2/2020 Harmouche
2020/0046429 A1* 2/2020 Tschida .............. A61B 18/1492
2020/0046949 A1 2/2020 Chisena et al.
2020/0054352 A1 2/2020 Brouillette et al.
2020/0060814 A1 2/2020 Murphy
2020/0061931 A1 2/2020 Brown et al.
2020/0069371 A1 3/2020 Brown et al.
2020/0085458 A1 3/2020 Nguyen et al.
2020/0085459 A1 3/2020 Adams
2020/0101269 A1 4/2020 Hayes
2020/0107960 A1 4/2020 Bacher
2020/0108236 A1 4/2020 Salazar et al.
2020/0129195 A1 4/2020 McGowan et al.
2020/0129741 A1 4/2020 Kawwas
2020/0138506 A1* 5/2020 Fraasch .............. A61B 18/1206
2020/0155812 A1 5/2020 Zhang et al.
2020/0197019 A1 6/2020 Harper
2020/0205890 A1 7/2020 Harlev
2020/0246032 A1 8/2020 Betelia et al.
2020/0289202 A1 9/2020 Miyagawa et al.
2020/0297366 A1 9/2020 Nguyen et al.
2020/0337717 A1 10/2020 Walzman
2020/0345380 A1 11/2020 Boyle et al.
2020/0383724 A1 12/2020 Adams et al.
2020/0397230 A1 12/2020 Massimini et al.
2020/0397453 A1 12/2020 McGowan et al.
2020/0398033 A1 12/2020 McGowan et al.
2020/0405333 A1 12/2020 Massimini et al.
2020/0405391 A1 12/2020 Massimini et al.
2020/0406009 A1 12/2020 Massimini et al.
2020/0406010 A1 12/2020 Massimini et al.
2021/0038237 A1 2/2021 Adams
2021/0085347 A1 3/2021 Phan et al.
2021/0085348 A1 3/2021 Nguyen
2021/0085383 A1 3/2021 Vo et al.
2021/0128241 A1 5/2021 Schultheis
2021/0137598 A1 5/2021 Cook
2021/0153939 A1 5/2021 Cook
2021/0177442 A1* 6/2021 Girdhar ................ A61B 17/221
2021/0177445 A1 6/2021 Nguyen
2021/0186613 A1 6/2021 Cook
2021/0212765 A1 7/2021 Verhagen
2021/0220052 A1 7/2021 Cook
2021/0220053 A1 7/2021 Cook
2021/0244473 A1 8/2021 Cook et al.
2021/0267685 A1 9/2021 Schultheis
2021/0275247 A1 9/2021 Schultheis
2021/0275249 A1 9/2021 Massimini et al.
2021/0282792 A1 9/2021 Adams et al.
2021/0290259 A1 9/2021 Hakala et al.
2021/0290286 A1 9/2021 Cook
2021/0290305 A1 9/2021 Cook
2021/0298603 A1 9/2021 Feldman
2021/0307828 A1 10/2021 Schultheis
2021/0330384 A1 10/2021 Cook
2021/0338258 A1 11/2021 Hawkins et al.
2021/0353359 A1 11/2021 Cook
2021/0369348 A1 12/2021 Cook
2021/0378743 A1 12/2021 Massimini et al.
2021/0378744 A1 12/2021 Fanier et al.
2021/0386479 A1 12/2021 Massimini et al.
2022/0000505 A1 1/2022 Hauser
2022/0000506 A1 1/2022 Hauser
2022/0000507 A1 1/2022 Hauser
2022/0000508 A1 1/2022 Schmitt et al.
2022/0000509 A1 1/2022 Laser et al.
2022/0000551 A1 1/2022 Govari et al.
2022/0001138 A1 1/2022 Howell
2022/0008130 A1 1/2022 Massimini et al.
2022/0008693 A1 1/2022 Humbert et al.
2022/0015785 A1 1/2022 Hakala et al.
2022/0021190 A1 1/2022 Pecquois
2022/0022902 A1 1/2022 Spano
2022/0022912 A1 1/2022 Efremkin
2022/0023528 A1 1/2022 Long et al.
2022/0040454 A1 2/2022 Hamm
2022/0054194 A1 2/2022 Bacher et al.
2022/0071704 A1 3/2022 Le
2022/0168594 A1 6/2022 Mayer
2022/0183738 A1 6/2022 Flores et al.
2022/0218402 A1 7/2022 Schultheis
2022/0249165 A1 8/2022 Cook
2022/0249166 A1 8/2022 Cook et al.
2022/0273324 A1 9/2022 Schultheis
2022/0313293 A1 10/2022 Singh
2022/0313359 A1 10/2022 Schultheis et al.
2022/0354578 A1 11/2022 Cook
2022/0387106 A1 12/2022 Cook
2023/0013920 A1 1/2023 Massimini
2023/0064371 A1 3/2023 Cook et al.
2023/0137107 A1 5/2023 Cook et al.
2023/0157754 A1 5/2023 Bacher et al.
2023/0200906 A1 6/2023 Cook et al.
2023/0233256 A1 7/2023 Cook et al.
2023/0240748 A1 8/2023 Cook et al.
2023/0255635 A1 8/2023 Schultheis et al.
2023/0255688 A1 8/2023 Schultheis et al.
2023/0255689 A1 8/2023 Schultheis et al.
2023/0310054 A1 10/2023 Schultheis
2023/0310067 A1 10/2023 Schultheis et al.
2023/0310073 A1 10/2023 Adams et al.
2023/0320576 A1 10/2023 Feldman
2023/0338088 A1 10/2023 Massimini et al.
2023/0338089 A1 10/2023 Schultheis
2024/0001076 A1 1/2024 Gelsinger
2024/0016508 A1 1/2024 Kocur
2024/0016544 A1 1/2024 Schultheis et al.
2024/0016545 A1 1/2024 Schultheis et al.
2024/0023813 A1 1/2024 Milner
2024/0032995 A1 2/2024 Schultheis et al.
2024/0033002 A1 2/2024 Cook
2024/0041520 A1 2/2024 Schultheis et al.
2024/0050170 A1 2/2024 Fournier
2024/0050696 A1 2/2024 Japuntich
2024/0058060 A1 2/2024 Cook et al.
2024/0065711 A1 2/2024 Hendrickson
2024/0099773 A1 3/2024 Schabert
2024/0165658 A1 5/2024 Fu
2024/0173044 A1 5/2024 Chen et al.
2024/0173526 A1 5/2024 Kofidis
2024/0189543 A1 6/2024 Salinas
2024/0216062 A1 7/2024 Cook
2024/0260981 A1 8/2024 Betelia
2024/0260982 A1 8/2024 Peterson
2024/0277410 A1 8/2024 Cook

(56) References Cited

U.S. PATENT DOCUMENTS

| | | | |
|---|---|---|---|
| 2024/0277974 | A1 | 8/2024 | Oehler |
| 2024/0277980 | A1 | 8/2024 | O'Neill |
| 2024/0285296 | A1 | 8/2024 | Vo |
| 2024/0285922 | A1 | 8/2024 | Chu |
| 2024/0299051 | A1 | 9/2024 | Sidhu et al. |
| 2024/0307119 | A1 | 9/2024 | Nguyen |
| 2024/0325045 | A1 | 10/2024 | Otake |
| 2024/0382258 | A1 | 11/2024 | Schultheis |
| 2025/0025237 | A1 | 1/2025 | Cook |
| 2025/0040947 | A1 | 2/2025 | Schultheis |

FOREIGN PATENT DOCUMENTS

| | | | |
|---|---|---|---|
| AU | 2021282522 | A1 | 1/2022 |
| AU | 2023210656 | A1 | 8/2023 |
| CA | 2229806 | | 3/1997 |
| CA | 2281519 | | 8/1998 |
| CA | 2983655 | | 10/2016 |
| CA | 3091389 | A1 | 10/2019 |
| CN | 102057422 | | 5/2011 |
| CN | 109223100 | | 1/2019 |
| CN | 110638501 | | 1/2020 |
| CN | 110638501 | A | 1/2020 |
| CN | 106794043 | | 3/2020 |
| CN | 111902100 | A | 11/2020 |
| CN | 11399346 | | 1/2022 |
| CN | 107411805 | | 1/2022 |
| CN | 107899126 | | 1/2022 |
| CN | 109475378 | | 1/2022 |
| CN | 113876388 | | 1/2022 |
| CN | 113877044 | | 1/2022 |
| CN | 113907838 | | 1/2022 |
| CN | 113951972 | A | 1/2022 |
| CN | 113951973 | A | 1/2022 |
| CN | 113974765 | | 1/2022 |
| CN | 113974826 | A | 1/2022 |
| CN | 215384399 | | 1/2022 |
| CN | 215386905 | | 1/2022 |
| CN | 215458400 | | 1/2022 |
| CN | 215458401 | | 1/2022 |
| CN | 215505065 | | 1/2022 |
| CN | 215534803 | | 1/2022 |
| CN | 215537694 | | 1/2022 |
| CN | 215584286 | | 1/2022 |
| CN | 215606068 | | 1/2022 |
| CN | 215651393 | | 1/2022 |
| CN | 215651394 | | 1/2022 |
| CN | 215651484 | | 1/2022 |
| CN | 215653328 | | 1/2022 |
| CN | 114053552 | | 2/2022 |
| CN | 117752412 | | 3/2024 |
| CN | 117958964 | A | 5/2024 |
| CN | 118055734 | | 5/2024 |
| DE | 3038445 | A1 | 5/1982 |
| DE | 3836337 | A | 4/1990 |
| DE | 3836337 | A1 | 4/1990 |
| DE | 3913027 | A1 | 10/1990 |
| DE | 69431758 | | 1/2003 |
| DE | 10230626 | | 1/2004 |
| DE | 202008016760 | | 3/2009 |
| DE | 102007046902 | | 4/2009 |
| DE | 102008034702 | | 1/2010 |
| DE | 102009007129 | | 8/2010 |
| DE | 202010009899 | | 11/2010 |
| DE | 102013201928 | | 8/2014 |
| DE | 102020117713 | | 1/2022 |
| EP | 0119296 | | 9/1984 |
| EP | 0261831 | B1 | 6/1992 |
| EP | 558297 | A2 | 9/1993 |
| EP | 0571306 | A1 | 11/1993 |
| EP | 0547146 | | 7/1995 |
| EP | 1179993 | A1 | 2/2002 |
| EP | 1946712 | | 7/2008 |
| EP | 1946712 | A1 | 7/2008 |
| EP | 1453566 | | 9/2008 |
| EP | 2157569 | | 2/2010 |
| EP | 2470248 | | 7/2012 |
| EP | 2879595 | | 6/2015 |
| EP | 2879595 | A1 | 6/2015 |
| EP | 2944264 | A1 | 6/2015 |
| EP | 3226795 | A1 | 10/2017 |
| EP | 3318204 | | 5/2018 |
| EP | 2879607 | | 2/2019 |
| EP | 3461438 | A1 | 4/2019 |
| EP | 3473195 | A1 | 4/2019 |
| EP | 2961463 | | 5/2019 |
| EP | 3240603 | | 5/2019 |
| EP | 3197381 | | 3/2020 |
| EP | 3643260 | A1 | 4/2020 |
| EP | 3773299 | A1 | 2/2021 |
| EP | 3240494 | | 3/2021 |
| EP | 3522812 | | 12/2021 |
| EP | 3076881 | B1 | 1/2022 |
| EP | 3932342 | | 1/2022 |
| EP | 3936140 | | 1/2022 |
| EP | 3960099 | | 3/2022 |
| EP | 4051154 | | 9/2022 |
| EP | 4129213 | | 2/2023 |
| EP | 4277537 | | 11/2023 |
| EP | 4146322 | | 4/2024 |
| EP | 3182931 | | 6/2024 |
| EP | 3950036 | | 8/2024 |
| EP | 4034005 | | 12/2024 |
| EP | 4602999 | A2 | 8/2025 |
| GB | 1082397 | | 9/1967 |
| IL | 277198 | A | 10/2020 |
| JP | S62275446 | A | 11/1987 |
| JP | H05264763 | | 10/1993 |
| JP | 1996089511 | | 4/1996 |
| JP | H09117407 | | 5/1997 |
| JP | 2001-517805 | A | 10/2001 |
| JP | 2001520070 | | 10/2001 |
| JP | 2004519296 | | 7/2004 |
| JP | 2008506447 | | 3/2008 |
| JP | 2008083273 | | 4/2008 |
| JP | 2009519777 | | 5/2009 |
| JP | 2009213589 | | 9/2009 |
| JP | 4805208 | | 11/2011 |
| JP | 4808620 | | 11/2011 |
| JP | 2012505050 | | 3/2012 |
| JP | 2012-510345 | A | 5/2012 |
| JP | 2014123147 | | 7/2014 |
| JP | A2014516614 | | 7/2014 |
| JP | A2015522344 | | 8/2015 |
| JP | 2018538077 | | 12/2018 |
| JP | 7177174 | B2 | 11/2022 |
| JP | 2022-180405 | A | 12/2022 |
| JP | 7512350 | B2 | 7/2024 |
| JP | 2024-114851 | A | 8/2024 |
| KR | 20050098932 | | 10/2005 |
| KR | 20080040111 | | 5/2008 |
| KR | 20160090877 | A | 8/2016 |
| KR | 20180054041 | | 5/2018 |
| KR | 10-2550642 | B1 | 7/2023 |
| KR | 10-2709378 | B1 | 9/2024 |
| KR | 10-2026-0009948 | A | 1/2026 |
| KR | 10-2907901 | B1 | 1/2026 |
| WO | WO9007904 | A1 | 7/1990 |
| WO | WO9105332 | A1 | 4/1991 |
| WO | 9203095 | A1 | 3/1992 |
| WO | WO9208515 | | 5/1992 |
| WO | 9902095 | A1 | 1/1999 |
| WO | 1999002095 | A1 | 1/1999 |
| WO | 9920189 | A1 | 4/1999 |
| WO | 1999020189 | A1 | 4/1999 |
| WO | WO200067648 | | 11/2000 |
| WO | WO2000067648 | A1 | 11/2000 |
| WO | WO0103599 | | 1/2001 |
| WO | WO0103599 | A2 | 1/2001 |
| WO | 20060006169 | A2 | 1/2006 |
| WO | WO2006006169 | | 1/2006 |
| WO | WO2009121017 | | 10/2009 |
| WO | WO2009149321 | A1 | 12/2009 |
| WO | WO2009152352 | A2 | 12/2009 |

(56) References Cited

FOREIGN PATENT DOCUMENTS

| | | | |
|---|---|---|---|
| WO | 2010042653 | A1 | 4/2010 |
| WO | WO2011094379 | | 8/2011 |
| WO | 20110126580 | A2 | 10/2011 |
| WO | WO2011126580 | A3 | 10/2011 |
| WO | WO2012025833 | | 3/2012 |
| WO | WO2012042619 | | 4/2012 |
| WO | WO20120052924 | A1 | 4/2012 |
| WO | WO2012058156 | | 5/2012 |
| WO | WO2012099974 | A2 | 7/2012 |
| WO | WO20120120495 | A2 | 9/2012 |
| WO | WO2013119662 | | 8/2013 |
| WO | 20130169807 | A1 | 11/2013 |
| WO | WO2013169807 | | 11/2013 |
| WO | WO2014022436 | A1 | 2/2014 |
| WO | WO2014025397 | A1 | 2/2014 |
| WO | WO20140022867 | A1 | 2/2014 |
| WO | WO2014138582 | | 9/2014 |
| WO | WO2015056662 | | 4/2015 |
| WO | WO2015097251 | A2 | 7/2015 |
| WO | 20150177790 | A1 | 11/2015 |
| WO | WO2016014999 | | 1/2016 |
| WO | WO2016089683 | A1 | 6/2016 |
| WO | WO2016090175 | | 6/2016 |
| WO | WO2016098670 | | 6/2016 |
| WO | WO2016109739 | | 7/2016 |
| WO | WO2016143556 | | 9/2016 |
| WO | WO2016151595 | A1 | 9/2016 |
| WO | WO2017004432 | A1 | 1/2017 |
| WO | WO20170192869 | A1 | 11/2017 |
| WO | 2017212404 | A1 | 12/2017 |
| WO | 20180022641 | A1 | 2/2018 |
| WO | WO2018022593 | A1 | 2/2018 |
| WO | WO2018083666 | | 5/2018 |
| WO | 20180175322 | A1 | 9/2018 |
| WO | WO2018175322 | | 9/2018 |
| WO | WO2018191013 | | 10/2018 |
| WO | 2019186564 | A1 | 10/2019 |
| WO | WO2019200201 | A1 | 10/2019 |
| WO | WO2019215869 | A1 | 11/2019 |
| WO | WO2019222843 | | 11/2019 |
| WO | WO2020056031 | | 3/2020 |
| WO | WO20200086361 | A1 | 4/2020 |
| WO | WO2020089876 | A1 | 5/2020 |
| WO | WO2020157648 | | 8/2020 |
| WO | WO2020256898 | | 12/2020 |
| WO | WO2020256898 | A1 | 12/2020 |
| WO | WO2020256949 | | 12/2020 |
| WO | WO2020256949 | A1 | 12/2020 |
| WO | WO2020263469 | A1 | 12/2020 |
| WO | WO2020263685 | A1 | 12/2020 |
| WO | WO2020263687 | A1 | 12/2020 |
| WO | WO2020263688 | A1 | 12/2020 |
| WO | WO2020263689 | A1 | 12/2020 |
| WO | WO2021061451 | | 4/2021 |
| WO | WO2021067563 | | 4/2021 |
| WO | WO2021086571 | A1 | 5/2021 |
| WO | WO2021096922 | A1 | 5/2021 |
| WO | WO2021101766 | | 5/2021 |
| WO | WO2021101766 | A1 | 5/2021 |
| WO | WO2021126762 | A1 | 6/2021 |
| WO | WO2021162855 | A1 | 8/2021 |
| WO | WO2021173417 | A1 | 9/2021 |
| WO | WO2021183367 | A1 | 9/2021 |
| WO | WO2021183401 | A1 | 9/2021 |
| WO | WO2021188233 | A1 | 9/2021 |
| WO | WO2021202248 | A1 | 10/2021 |
| WO | WO2021231178 | A1 | 11/2021 |
| WO | WO2021247685 | A1 | 12/2021 |
| WO | WO2021257425 | A1 | 12/2021 |
| WO | WO2022007490 | | 1/2022 |
| WO | WO2022008440 | | 1/2022 |
| WO | WO2022010767 | A1 | 1/2022 |
| WO | WO2022055784 | | 3/2022 |
| WO | WO2022125525 | | 6/2022 |
| WO | WO2022154954 | | 7/2022 |
| WO | WO2022173719 | | 8/2022 |
| WO | WO2022187058 | | 9/2022 |
| WO | WO2022216488 | | 10/2022 |
| WO | WO2022240674 | | 11/2022 |
| WO | WO2022260932 | | 12/2022 |
| WO | WO2023107334 | | 6/2023 |
| WO | WO2024079108 | | 4/2024 |
| WO | WO2024107418 | | 5/2024 |

OTHER PUBLICATIONS

International Search Report and Written Opinion dated Apr. 4, 2022 in PCT Application Serial No. PCT/US2021/062170.

International Search Report and Written Opinion dated Apr. 4, 2022 in PCT Application Serial No. PCT/US2021/065073.

Partial Search Report and Provisional Opinion dated May 3, 2022 in PCT Application No. PCT/US2022/015577.

International Search Report and Written Opinion dated May 13, 2022 in PCT Application Serial No. PCT/US2022/017562.

International Search Report and Written Opinion dated Jul. 13, 2021 in PCT Application Serial No. PCT/US2021/024216.

International Search Report and Written Opinion dated Jun. 22, 2021 in PCT Application Serial No. PCT/US2021/020937.

International Search Report and Written Opinion dated Jun. 24, 2021 in PCT Application Serial No. PCT/US2021/021272.

International Search Report and Written Opinion dated Jun. 28, 2022, in PCT Application Serial No. PCT/US2022/015577.

International Search Report and Written Opinion dated Jun. 27, 2022, in PCT Application Serial No. PCT/US2022/022460.

Medlight, "Cylindrical light diffuser Model RD-ML", Medlight S.A., Switzerland. 2015. (This reference was cited in a prior Information Disclosure Statement. However, the relevant date was missing. The date has now been added.).

Medlight, "Cylindircal light diffuser Model RD", Medlight S.A., Switzerland. 2015. (This reference was cited in a prior Information Disclosure Statement. However, the relevant date was missing. The date has now been added.).

Ohl, Siew-Wan, et al. "Bubbles with shock waves and ultrasound: a review", Interface Focus, pp. 1-15, vol. 5, The Royal Society Publishing. Oct. 2015. This reference was cited in a prior Information Disclosure Statement. However, the relevant date was missing. The date has now been added.).

Schafter+Kirchhoff, Laser Beam Couplers series 60SMS for coupling into single-mode and polarization-maintaining fiber cables, Schafter+Kirchhoff, pp. 1-5, Germany. Dec. 2, 2021. (This reference was cited in a prior Information Disclosure Statement. However, the relevant date was missing. The date has now been added.).

Meng et al., "Accurate Recovery Of Atrial Endocardial Potential Maps From Non-contact Electrode Data." Auckland Bioengineering Institute. (ID 1421). May 2019. (This reference was cited in a prior Information Disclosure Statement. However, the relevant date was missing. The date has now been added.).

Jiang et al., "Multielectrode Catheter For Substrate Mapping For Scar-related VT Ablation: A Comparison Between Grid Versus Linear Configurations." UChicago Medicine, Center for Arrhythmia Care, Chicago IL (ID 1368). Poster for conference in San Francisco, May 8-11, 2019. (This reference was cited in a prior Information Disclosure Statement. However, the relevant date was missing. The date has now been added.).

Sacher et al., "Comparison Of Manual Vs Automatic Annotation To Identify Abnormal Substrate For Scar Related VT Ablation." LIRYC Institute, Bordeaux University Hospital, France (ID 1336). Poster for conference in San Francisco, May 8-11, 2019. (This reference was cited in a prior Information Disclosure Statement. However, the relevant date was missing. The date has now been added.).

International Search Report and Written Opinion dated Aug. 25, 2022 in PCT Application Serial No. PCTUS/2022/028035.

International Search Report and Written Opinion dated Sep. 15, 2022 in PCT Application Serial No. PCTUS/2022/032045.

International Search Report and Written Opinion dated Aug. 20, 2021 in PCT Application Serial No. PCT/US2021/031130.

International Search Report and Written Opinion, issued by the European Patent Office for PCT/2021/XXX, dated Sep. 30, 2021.

(56) References Cited

OTHER PUBLICATIONS

International Search Report and Written Opinion, PCT Application Serial No. PCT/US2022/047751 issued Feb. 10, 2023, by the European Patent Office. (56PCT).
International Search Report and Written Opinion, issued by the EP/ISA, in PCT/US2021/048819, dated Jan. 14, 2022.
AccuCoat, "Beamsplitter: Divide, combine & conquer"; 2023.
Lin et al., "Photoacoustic imaging", Science Direct; 2021.
Zhou et al., "Photoacoustic Imaging with fiber optic technology: A review", Science Direct; 2020.
International Search Report and Written Opinion issued by the European Patent Office, for Serial No. PCT/US2022/053775, dated Apr. 21, 2023. (Re 45PCT).
International Search Report and Written Opinion issued by the European Patent Office, for Serial No. PCT/US2023/011497, dated Apr. 28, 2023. (Re 54PCT).
International Search Report and Written Opinion issued by the European Patent Office, for Serial No. PCT/US2023/012599, dated May 19, 2023. (Re 57PCT).
International Preliminary Report on Patentability dated Sep. 15, 2020 in PCT Application Serial No. PCT/US2019/022009.
International Search Report and Written Opinion dated Sep. 14, 2020 in PCT Application Serial No. PCT/US2020/038523.
International Search Report and Written Opinion dated Oct. 2, 2020 in PCT Application Serial No. PCT/US2020/036107.
Schafter+Kirchhoff, Laser Beam Couplers series 60SMS for coupling into single-mode and polarization-maintaining fiber cables, Schafter+Kirchhoff, pp. 1-5, Germany.
International Search Report and Written Opinion dated Jan. 29, 2020 in PCT Application Serial No. PCT/US2020/059961.
International Search Report and Written Opinion dated Jan. 20, 2020 in PCT Application Serial No. PCT/US2020/054792.
Partial Search Report and Provisional Opinion dated Feb. 19, 2021 in PCT Application Serial No. PCT/US2020/059960.
Shariat, Mohammad H., et al. "Localization of the ectopic spiral electrical source using intracardiac electrograms during atrial fibrillation." 2015 IEEE 28th Canadian Conference on Electrical and Computer Engineering (CCECE). IEEE, 2015.
Nademanee, Koonlawee, et al. "A new approach for catheter ablation of atrial fibrillation: mapping of the electrophysiologic substrate." Journal of the American College of Cardiology 43.11 (2004): 2044-2053.
Calkins, Hugh. "Three dimensional mapping of atrial fibrillation: techniques and necessity." Journal of interventional cardiac electrophysiology 13.1 (2005): 53-59.
Shariat, Mohammad Hassan. Processing the intracardiac electrogram for atrial fibrillation ablation. Diss. Queen's University (Canada), 2016.
Meng et al., "Accurate Recovery Of Atrial Endocardial Potential Maps From Non-contact Electrode Data." Auckland Bioengineering Institute. (ID 1421).
Jiang et al., "Multielectrode Catheter For Substrate Mapping For Scar-related VT Ablation: A Comparison Between Grid Versus Linear Configurations." UChicago Medicine, Center for Arrhythmia Care, Chicago IL (ID 1368).
Sacher et al., "Comparison Of Manual Vs Automatic Annotation To Identify Abnormal Substrate For Scar Related VT Ablation." LIRYC Institute, Bordeaux University Hospital, France (ID 1336).
Oriel Instruments, "Introduction to Beam Splitters for Optical Research Applications", Apr. 2014, pp. 1-9, https://www.azoptics.com/Article.aspx?ArticaID=871.
International Search Report and Written Opinion dated Apr. 12, 2021 in PCT Application Serial No. PCT/US2020/059960.
International Search Report and Written Opinion dated Apr. 13, 2021 in PCT Application Serial No. PCT/US2020/064846.
International Search Report and Written Opinion dated Apr. 13, 2021 in PCT Application Serial No. PCT/US2021/013944.
International Search Report and Written Opinion dated May 25, 2021 in PCT Application Serial No. PCT/US2021/017604.
International Search Report and Written Opinion dated Jun. 2, 2021 in PCT Application Serial No. PCT/US2021/018522.
International Search Report and Written Opinion dated Jun. 2, 2021 in PCT Application Serial No. PCT/US2021/015204.
International Search Report and Written Opinion dated Jun. 17, 2021 in PCT Application Serial No. PCT/US2021/020934.
Stelzle, F., et al. "Diffuse Reflectance Spectroscopy for Optical Soft Tissue Differentiation as Remote Feedback Control for Tissue-Specific Laser Surgery", Lasers in Surgery and Medicine, 2010, pp. 319-325, vol. 42, Wiley-Liss Inc.
Stelzle, F., et al. Tissue Discrimination by Uncorrected Autofluorescence Spectra: A Proof-of-Principle Study for Tissue-Specific Laser Surgery, Sensors, 2013, pp. 13717-13731, vol. 13, Basel, Switzerland.
Tagawa, Y., et al. "Structure of laser-induced shock wave in water", Japan Society for the Promotion of Science, 2016.
Shen, Y., et al. "Theoretical and experimental studies of directivity of sound field generated by pulsed laser induced breakdown in liquid water", SPIE, 2013, pp. 8796141-8796148, vol. 8796, SPIE.
Preisack, M., et al. "Ultrafast imaging of tissue ablation by a XeCl excimer laser in saline", Lasers in Surgery and Medicine, 1992, pp. 520-527, vol. 12, Wiley-Liss Inc.
Versluis, M., et al. "How Snapping Shrimp Snap: Through Cavitating Bubbles", Science Mag, 2000, pp. 2114-2117, vol. 289, American Association for the Advancement of Science, Washington DC, USA.
Yan, D., et al. "Study of the Electrical Characteristics, Shock-Wave Pressure Characteristics, and Attenuation Law Based on Pulse Discharge in Water", Shock and Vibration, 2016, pp. 1-11, vol. 2016, Article ID 6412309, Hindawi Publishing Corporation.
Zhang, Q., et al. "Improved Instruments and Methods for the Photographic Study of Spark-Induced Cavitation Bubbles", Water, 2018, pp. 1-12, vol. 10, No. 1683.
"Damage threshold of fiber facets", NKT Photonics, 2012, pp. 1-4, Denmark.
Smith, A., et al. "Bulk and surface laser damage of silica by picosecond and nanosecond pulses at 1064 nm", Applied Optics, 2008, pp. 4812-4832, vol. 47, No. 26, Optical Society of America.
Smith, A., et al. "Deterministic Nanosecond Laser-Induced Breakdown Thresholds In Pure and Yb3 Doped Fused Silica", SPIE, 2007, pp. 6453171-64531712, vol. 6453, SPIE.
Sun, X., et al. "Laser Induced Damage to Large Core Optical Fiber by High Peak Power Laser", Specialty Photonics Division, 2010.
Smith, A., et al. "Nanosecond laser-induced breakdown in pure and Yb3 doped fused silica", SPIE, 2007, vol. 6403, SPIE.
Smith, A., et al. "Optical Damage Limits to Pulse Energy From Fibers", IEEE Journal of Selected Topics in Quantum Electronics, 2009, pp. 153-158, vol. 15, No. 1, IEEE.
Reichel, E., et al. "A Special Irrigation Liquid to Increase the Reliability of Laser-Induced Shockwave Lithotripsy", Lasers in Surgery and Medicine, 1992, pp. 204-209, vol. 12, Wiley-Liss Inc., Graz, Austria.
Reichel, E., et al. "Bifunctional irrigation liquid as an ideal energy converter for laser lithotripsy with nanosecond laser pulses", SPIE Lasers in Urology, Laparoscopy, and General Surgery, 1991, pp. 129-133, vol. 1421, SPIE.
Reichel, E., et al. "Laser-induced Shock Wave Lithotripsy with a Regenerative Energy Converter", Lasers in Medical Science, 1992, pp. 423-425, vol. 7, Bailliere Tindall.
Hardy, L., et al. "Cavitation Bubble Dynamics during Thulium Fiber Laser Lithotripsy", SPIE BiOS, 2016, vol. 9689, SPIE.
Deckelbaum, L., "Coronary Laser Angioplasty", Lasers in Surgery and Medicine, 1994, pp. 101-110, vol. 14, Wiley-Liss Inc., Conneticuit, USA.
Shangguan, H., et al. "Effects of Material Properties on Laser-induced Bubble Formation in Absorbing Liquids and On Submerged Targets", Diagnostic and Therapeutic Cardiovascular Interventions VII, SPIE, 1997, pp. 783-791, vol. 2869, SPIE.
Van Leeuwen, T., et al. "Excimer Laser Induced Bubble: Dimensions, Theory, and Implications for Laser Angioplasty", Lasers in Surgery and Medicine, 1996, pp. 381-390, vol. 18, Wiley-Liss Inc., The Netherlands.

(56) References Cited

OTHER PUBLICATIONS

Vogel, A., et al. "Minimization of Cavitation Effects in Pulsed Laser Ablation Illustrated on Laser Angioplasty", Applied Physics, 1996, pp. 173-182, vol. 62, Springer-Verlag.
Vogel, A., et al. "Shock Wave Emission and Cavitation Bubble Generation by Picosecond and Nanosecond Optical Breakdown in Water", The Journal of Acoustical Society of America, 1996, pp. 148-165, vol. 100, No. 1, The Acoustical Society of America.
Varghese, B., et al. "Influence of absorption induced thermal initiation pathway on irradiance threshold for laser induced breakdown", Biomedical Optics Express, 2015, vol. 6, No. 4, Optical Society of America.
Linz, N., et al. "Wavelength dependence of nanosecond infrared laser-induced breakdown in water: Evidence for multiphoton initiation via an intermediate state", Physical Review, 2015, pp. 134114.1-1341141.10, vol. 91, American Physical Society.
International Search Report and Written Opinion dated Jun. 27, 2018, in PCT Application Serial No. PCT/US2018/027121.
International Search Report and Written Opinion dated Jul. 20, 2018, in PCT Application Serial No. PCT/US2018/027801.
International Search Report and Written Opinion dated Jul. 20, 2018, in PCT Application Serial No. PCT/US2018/027784.
European Search Report, for European Patent Application No. 18185152, mailed Dec. 13, 2018.
International Search Report and Written Opinion dated May 22, 2019, in PCT Application Serial No. PCT/US2019/022009.
International Search Report and Written Opinion dated May 29, 2019, in PCT Application Serial No. PCT/US2019/022016.
International Search Report and Written Opinion dated Jun. 22, 2018, in Application Serial No. NL2019807, issued by the European Patent Office.
Noimark, Sacha, et al., "Carbon-Nanotube-PDMS Composite Coatings on Optical Fibers for All-Optical Ultrasound Imaging", Advanced Functional Materials, 2016, pp. 8390-8396, vol. 26, Wiley-Liss Inc.
Chen, Sung-Liang, "Review of Laser-Generated Ultrasound Transmitters and their Applications to All-Optical Ultrasound Transducers and Imaging", Appl. Sci. 2017, 7, 25.
Colchester, R., et al. "Laser-Generated ultrasound with optica fibres using functionalised carbon nanotube composite coatings", Appl. Phys. Lett., 2014, vol. 104, 173504, American Institute of Physics.
Poduval, R., et al. "Optical fiber ultrasound transmitter with electrospun carbon nanotube-polymer composite", Appl. Phys. Lett., 2017, vol. 110, 223701, American Institute of Physics.
Tian, J., et al. "Distributed fiber-optic laser-ultrasound generation based on ghost-mode of tilted fiber Bragg gratings", Optics Express, Mar. 2013, pp. 6109-6114, vol. 21, No. 5, Optical Society of America.
Kim, J., et al. "Optical Fiber Laser-Generated-Focused-Ultrasound Transducers for Intravascular Therapies", IEEE, 2017.
Kang, H., et al. "Enhanced photocoagulation with catheter-based diffusing optical device", Journal of Biomedical Optics, 2012, vol. 17, Issue 11, 118001, SPIE.
International Search Report and Written Opinion dated Jan. 3, 2020, in PCT Application Serial No. PCT/US2019/056579.
Communication Pursuant to Article 94(3) EPC, for European Patent Application No. 18185152.8, mailed Jan. 16, 2019.
European Search Report, for European Patent Application No. 18185152.8, mailed Dec. 20, 2018.
International Search Report and Written Opinion dated Jul. 29, 2020 in PCT Application Serial No. PCT/US2020/034005.
International Search Report and Written Opinion dated Sep. 11, 2020 in PCT Application Serial No. PCT/US2020/038517.
International Search Report and Written Opinion dated Sep. 9, 2020 in PCT Application Serial No. PCT/US2020/038530.
International Search Report and Written Opinion dated Sep. 11, 2020 in PCT Application Serial No. PCT/US2020/038521.
International Search Report and Written Opinion dated Sep. 7, 2020 in PCT Application Serial No. PCT/US2020/034642.
Vogel, A., et al. "Intraocular Photodisruption With Picosecond and Nanosecond Laser Pulses: Tissue Effects in Cornea, Lens, and Retina", Investigative Ophthalmology & Visual Science, Jun. 1994, pp. 3032-3044, vol. 35, No. 7, Association for Research in Vision and Ophthalmology.
Jones, H. M., et al. "Pulsed dielectric breakdown of pressurized water and salt solutions", Journal of Applied Physics, Jun. 1998, pp. 795-805, vol. 77, No. 2, American Institute of Physics.
Kozulin, I., et al. "The dynamic of the water explosive vaporization on the flat microheater", Journal of Physics: Conference Series, 2018, pp. 1-4, IOP Publishing, Russia.
Cross, F., "Laser Angioplasty", Vascular Medicine Review, 1992, pp. 21-30, Edward Arnold.
Doukas, A. G., et al. "Laser-generated stress waves and their effects on the cell membrane", IEEE Journal of Selected Topics in Quantum Electronics, 1999, pp. 997-1003, vol. 5, Issue 4, IEEE.
Noack, J., et al. "Laser-Induced Plasma Formation in Water at Nanosecond to Femtosecond Time Scales: Calculation of Thresholds, Absorption Coefficients, and Energy Density", IEEE Journal of Quantum Electronics, 1999, pp. 1156-1167, vol. 35, No. 8, IEEE.
Pratsos, A., "The use of Laser for the treatment of coronary artery disease", Bryn Mawr Hospital, 2010.
Li, Xian-Dong, et al. "Influence of deposited energy on shock wave induced by underwater pulsed current discharge", Physics of Plasmas, 2016, vol. 23, American Institute of Physics.
Logunov, S., et al. "Light diffusing optical fiber illumination", Renewable Energy and the Environment Congress, 2013, Corning, NY, USA.
Maxwell, A. D., et al. "Cavitation clouds created by shock scattering from bubbles during histotripsy", Acoustical Society of America, 2011, pp. 1888-1898, vol. 130, No. 4, Acoustical Society of America.
Mcateer, James A., et al. "Ultracal-30 Gypsum Artificial Stones For Research On The Mechinisms Of Stone Breakage In Shock Wave Lithotripsy", 2005, pp. 429-434, Springer-Verlag.
Vogel, A., et al. "Mechanisms of Intraocular Photodisruption With Picosecond and Nanosecond Laser Pulses", Lasers in Surgery and Medicine, 1994, pp. 32-43, vol. 15, Wiley-Liss Inc., Lubeck, Germany.
Vogel, A., et al. "Mechanisms of Pulsed Laser Ablation of Biological Tissues", Chemical Reviews, 2003, pp. 677-644, vol. 103, No. 2, American Chemical Society.
Medlight, "Cylindrical light diffuser Model RD-ML", Medlight S.A., Switzerland.
Medlight, "Cylindircal light diffuser Model RD", Medlight S.A., Switzerland.
Mayo, Michael E., "Interaction of Laser Radiation with Urinary Calculi", Cranfield University Defense and Security, PhD Thesis, 2009, Cranfield University.
Mirshekari, G., et al. "Microscale Shock Tube", Journal of Microelectromechanical Systems, 2012, pp. 739-747, vol. 21, No. 3, IEEE.
"Polymicro Sculpted Silica Fiber Tips", Molex, 2013, Molex.
Zhou, J., et al. "Optical Fiber Tips and Their Applications", Polymicro Technologies A Subsidiary of Molex, Nov. 2007.
Liang, Xiao-Xuan, et al. "Multi-Rate-Equation modeling of the energy spectrum of laser-induced conduction band electrons in water", Optics Express, 2019, vol. 27, No. 4, Optical Society of America.
Nachabe, R., et al. "Diagnosis of breast cancer using diffuse optical spectroscopy from 500 to 1600 nm: comparison of classification methods", Journal of Biomedical Optics, 2011, vol. 16(8), SPIE.
Naugol'nykh, K. A., et al. "Spark Discharges in Water", Academy of Sciences USSR Institute of Acoustics, 1971, Nauka Publishing Co., Moscow, USSR.
Van Leeuwen, Ton G., et al. "Noncontact Tissue Ablation by Holmium: YSGG Laser Pulses in Blood", Lasers in Surgery and Medicine, 1991, vol. 11, pp. 26-34, Wiley-Liss Inc.
Nyame, Yaw A., et al. "Kidney Stone Models for In Vitro Lithotripsy Research: A Comprehensive Review", Journal of Endourology, Oct. 2015, pp. 1106-1109, vol. 29, No. 10, Mary Ann Liebert Inc., Cleveland, USA.
Ohl, Siew-Wan, et al. "Bubbles with shock waves and ultrasound: a review", Interface Focus, pp. 1-15, vol. 5, The Royal Society Publishing.

(56) References Cited

OTHER PUBLICATIONS

Zheng, W., "Optical Lenses Manufactured on Fiber Ends", IEEE, 2015, Splicer Engineering, Duncan SC USA.
Dwyer, P. J., et al. "Optically integrating balloon device for photodynamic therapy", Lasers in Surgery and Medicine, 2000, pp. 58-66, vol. 26, Issue 1, Wiley-Liss Inc., Boston MA USA.
"The New Optiguide DCYL700 Fiber Optic Diffuser Series", Optiguide Fiber Optic Spec Sheet, Pinnacle Biologics, 2014, Pinnacle Biologics, Illinois, USA.
Van Leeuwen, Ton G., et al. "Origin of arterial wall dissections induced by pulsed excimer and mid-infared laser ablation in the pig", JACC, 1992, pp. 1610-1618, vol. 19, No. 7, American College of Cardiology.
Oshita, D., et al. "Characteristic of Cavitation Bubbles and Shock Waves Generated by Pulsed Electric Discharges with Different Voltages", IEEE, 2012, pp. 102-105, Kumamoto, Japan.
Karsch, Karl R., et al. "Percutaneous Coronary Excimer Laser Angioplasty in Patients With Stable and Unstable Angina Pectoris", Circulation, 1990, pp. 1849-1859, vol. 81, No. 6, American Heart Association, Dallas TX, USA.
Murray, A., et al. "Peripheral laser angioplasty with pulsed dye laser and ball tipped optical fibres", The Lancet, 1989, pp. 1471-1474, vol. 2, Issue 8678-8679.
Mohammadzadeh, M., et al. "Photoacoustic Shock Wave Emission and Cavitation from Structured Optical Fiber Tips", Applied Physics Letters, 2016, vol. 108, American Institute of Physics Publishing LLC.
Doukas, A. G., et al. "Physical characteristics and biological effects of laser-induced stress waves", Ultrasound in Medicine and Biology, 1996, pp. 151-164, vol. 22, Issue 2, World Federation for Ultrasound in Medicine and Biology, USA.
Doukas, A. G., et al. "Physical factors involved in stress-wave-induced cell injury: the effect of stress gradient", Ultrasound in Medicine and Biology, 1995, pp. 961-967, vol. 21, Issue 7, Elsevier Science Ltd., USA.
Piedrahita, Francisco S., "Experimental Research Work On A Sub-Millimeter Spark-Gap For Sub Nanosecond Gas Breakdown", Thesis for Universidad Nacional De Colombia, 2012, Bogota, Colombia.
Vogel, A., et al. "Plasma Formation in Water by Picosecond and Nanosecond Nd: YAG Laser Pulses—Part I: Optical Breakdown at Threshold and Superthreshold Irradiance", IEEE Journal of Selected Topics in Quantum Electronics, 1996, pp. 847-859, vol. 2, No. 4, IEEE.
Park, Hee K., et al. "Pressure Generation and Measurement in the Rapid Vaporization of Water on a Pulsed-Laser-Heated Surface", Journal of Applied Physics, 1996, pp. 4072-4081, vol. 80, No. 7, American Institute of Physics.
Cummings, Joseph P., et al. "Q-Switched laser ablation of tissue: plume dynamics and the effect of tissue mechanical properties", SPIE, Laser-Tissue Interaction III, 1992, pp. 242-253, vol. 1646.
Lee, Seung H., et al. "Radial-firing optical fiber tip containing conical-shaped air-pocket for biomedical applications", Optics Express, 2015, vol. 23, No. 16, Optical Society of America.
Hui, C., et al. "Research on sound fields generated by laser-induced liquid breakdown", Optica Applicata, 2010, pp. 898-907, vol. XL, No. 4, Xi'an, China.
Riel, Louis-Philippe, et al. "Characterization of Calcified Plaques Retrieved From Occluded Arteries and Comparison with Potential Artificial Analogues", Proceedings of the ASME 2014 International Mechanical Engineering Congress and Exposition, 2014, pp. 1-11, ASME, Canada.
Roberts, Randy M., et al. "The Energy Partition of Underwater Sparks", The Journal of the Acoustical Society of America, 1996, pp. 3465-3475, vol. 99, No. 6, Acoustical Society of America.
Rocha, R., et al. "Fluorescence and Reflectance Spectroscopy for Identification of Atherosclerosis in Human Carotid Arteries Using Principal Components Analysis", Photomedicine and Lsser Surgery, 2008, pp. 329-335, vol. 26, No. 4, Mary Ann Liebert Inc.
Scepanovic, Obrad R., et al. "Multimodal spectroscopy detects features of vulnerable atherosclerotic plaque", Journal of Biomedical Optics, 2011, pp. 1-10, vol. 16, No. 1, SPIE.
Serruys, P. W., et al. "Shaking and Breaking Calcified Plaque Lithoplasty, a Breakthrough in Interventional Armamentarium?", JACC: Cardiovascular Imaging, 2017, pp. 907-911, vol. 10, No. 8, Elsevier.
Vogel, A., et al. "Shock wave emission and cavitation bubble generation by picosecond and nanosecond optical breakdown in water", The Journal of the Acoustical Society of America, 1996, pp. 148-165, vol. 100, No. 1, Acoustical Society of America.
Vogel, A., et al. "Shock-Wave Energy and Acoustic Energy Dissipation After Laser-induced Breakdown", SPIE, 1998, pp. 180-189, vol. 3254, SPIE.
Shen, Yajie et al. "High-peak-power and narrow-linewidth Q-switched Ho: YAG laser in-band pumped at 1931 nm." Applied Physics Express 13.5 (2020): 052006. (Year 2020).
PathFinder Digital, "Free Space Optics vs. Fiber Optics", 2023.
International Search Report and Written Opinion, issued in Application Serial No. PCT/US2023/016152, dated Jul. 12, 2023.
Definition of ablation—NCI Dictionary of Cancer Terms—NCI, National Cancer Institute, p. 1 (Year:2025).
Daemen, J., Tovar Forero, M.N, "The Coronary Intravascular Lithotripsy System", ICR Journal, 2019; 14(3); 174-181.
Butt, N., Khalid, N., Shlofmitz, E., "Intravascular Lithotripsy"; NCBI Bookshelf. A service of the National Library of Medicine, National Institutes of Health; StatPearls Publishing, 2023.
Davletshin, Yevgeniy R., "A Computational Analysis of Nanoparticle-Mediated Optical Breakdown", A dissertation presented to Ryerson University in Partial Fulfillment of the requirements for the degree of Doctor of Philosophy in the Program of Physics, Toronto, Ontario, CA 2017.
Vogel, A., et al. "Acoustic transient generation by laser-produced cavitation bubbles near solid boundaries", Journal Acoustical Society of America, 1988, pp. 719-731, vol. 84.
Asshauer, T., et al. "Acoustic transient generation by holmium-laser-induced cavitation bubbles", Journal of Applied Physics, Nov. 1, 1994, pp. 5007-5013, vol. 76, No. 9, American Institute of Physics.
Zheng, W., "Optic Lenses Manufactured on Fiber Ends", 2015, Splicer Engineering AFL, Duncan, SC USA.
Ali, Ziad A., et al. "Optical Coherence Tomography Characterization of Coronary Lithoplasty for Treatment of Calcified Lesions", JACC: Cardiovascular Imaging, 2017, pp. 897-906, vol. 109, No. 8, Elsevier.
Ali, Ziad A., et al. "Intravascular lithotripsy for treatment of stent underexpansion secondary to severe coronary calcification" 2018, European Society of Cardiology.
Ashok, Praveen C., et al. "Raman spectroscopy bio-sensor for tissue discrimination in surgical robotics—full article", Journal of Biophotonics, 2014, pp. 103-109, vol. 7, No. 1-2.
Ashok, Praveen C., et al. "Raman spectroscopy bio-sensor for tissue discrimination in surgical robotics—proof" Journal of Biophotonics 7, 2014, No. 1-2.
Bian, D. C., et al. "Experimental Study of Pulsed Discharge Underwater Shock-Related Properties in Pressurized Liquid Water", Hindawi Advances in Materials Science and Engineering, Jan. 2018, 12 pages, vol. 2018, Article ID 8025708.
Bian, D. C., et al. "Study on Breakdown Delay Characteristics Based on High-voltage Pulse Discharge in Water with Hydrostatic Pressure", Journal of Power Technologies 97(2), 2017, pp. 89-102.
Doukas, A. G., et al. "Biological effects of laser induced shock waves: Structural and functional cell damage in vitro", Ultrasound in Medicine and Biology, 1993, pp. 137-146, vol. 19, Issue 2, Pergamon Press, USA.
Brodmann, Marianne et al. "Safety and Performance of Lithoplasty for Treatment of Calcified Peripheral Artery Lesions", JACC, 2017, vol. 70, No. 7.
Brouillette, M., "Shock Waves at Microscales", 2003, pp. 3-12, Springer-Verlag.
Mirshekari, G., et al. "Shock Waves in Microchannels", 2013, pp. 259-283, vol. 724, Cambridge University Press.

(56) References Cited

OTHER PUBLICATIONS

"Bubble Dynamics and Shock Waves", Springer, 2013, Springer-Verlag, Berlin Heildelberg.
Hardy, Luke A., et al. "Cavitation Bubble Dynamics During Thulium Fiber Laser Lithotripsy", SPIE, Feb. 29, 2016, vol. 9689, San Francisco, California, USA.
Claverie, A., et al. "Experimental characterization of plasma formation and shockwave propagation induced by high power pulsed underwater electrical discharge", Review of Scientific Instruments, 2014, American Institute of Physics.
Blackmon, Richard L., et al. "Comparison of holmium: YAG and thulium fiber laser lithotripsy ablation thresholds, ablation rates, and retropulsion effects", Journal of Biomedical Optics, 2011, vol. 16(7), SPIE.
Debasis, P., et al. "Continuous-wave and quasi-continuous wave thulium-doped all-fiber laser: implementation on kidney stone fragmentations", Applied Optics, Aug. 10, 2016, vol. 55, No. 23, Optical Society of America.
Cook, Jason R., et al. "Tissue mimicking phantoms for photoacoustic and ultrasonic imaging", Biomedical Optics Express, 2011, vol. 2, No. 11, Optical Society of America.
Deckelbaum, Lawrence I., "Coronary Laser Angioplasty", Lasers in Surgery and Medicine, 1994, pp. 101-110, Wiley-Liss Inc.
Costanzo, F., "Underwater Explosion Phenomena and Shock Physics", Research Gate, 2011.
Mizeret, J. C., et al. "Cylindrical fiber optic light diffuser for medical applications", Lasers in Surgery and Medicine, 1996, pp. 159-167, vol. 19, Issue 2, Wiley-Liss Inc., Lausanne, Switzerland.
De Silva, K., et al. "A Calcific, Undilatable Stenosis Lithoplasty, a New Tool in the Box?", JACC: Cardiovascular Interventions, 2017, vol. 10, No. 3, Elsevier.
Vesselov, L., et al. "Design and performance of thin cylindrical diffusers created in Ge-doped multimode optical fibers", Applied Optics, 2005, pp. 2754-2758, vol. 44, Issue 14, Optical Society of America.
Hutchens, Thomas C., et al. "Detachable fiber optic tips for use in thulium fiber laser lithotripsy", Journal of Biomedical Optics, Mar. 2013, vol. 18(3), SPIE.
Kostanski, Kris L., et al. "Development of Novel Tunable Light Scattering Coating Materials for Fiber Optic Diffusers In Photodynamic Cancer Therapy", Journal of Applied Polymer Science, 2009, pp. 1516-1523, vol. 112, Wiley InterScience.
Kristiansen, M., et al. "High Voltage Water Breakdown Studies", DoD, 1998, Alexandria, VA, USA.
Dwyer, J. R., et al. "A study of X-ray emission from laboratory sparks in air at atmospheric pressure", Journal of Geophysical Research, 2008, vol. 113, American Geophysical Union.
Jansen, Duco E., et al. "Effect of Pulse Duration on Bubble Formation and Laser-Induced Pressure Waves During Holmium Laser Ablation", Lasers in Surgery and Medicine 18, 1996, pp. 278-293, Wiley-Liss Inc., Austin, TX, USA.
Shangguan, HanQun et al. "Effects of Material Properties on Laser-induced Bubble Formation in Absorbing Liquids and On Submerged Targets", SPIE, 1997, pp. 783-791, vol. 2869.
Varghese, B., et al. "Effects of polarization and absorption on laser induced optical breakdown threshold for skin rejuvenation", SPIE, Mar. 9, 2016, vol. 9740, SPIE, San Francisco, USA.
Varghese, B., et al. "Effects of polarization and apodization on laser induced optical breakdown threshold", Optics Express, Jul. 29, 2013, vol. 21, No. 15, Optical Society of America.
Bonito, Valentina, "Effects of polarization, plasma and thermal initiation pathway on irradiance threshold of laser induced optical breakdown", Philips Research, 2013, The Netherlands.
Vogel, A. et al. "Energy balance of optical breakdown in water at nanosecond to femtosecond time scales", Applied Physics B 68, 1999, pp. 271-280, Springer-Verlag.
Kang, Hyun W., et al. "Enhanced photocoagulation with catheter based diffusing optical device", Journal of Biomedical Optics, Nov. 2012, vol. 17(11), SPIE.
Esch, E., et al. "A Simple Method For Fabricating Artificial Kidney Stones Of Different Physical Properties", National Institute of Health Public Access Author Manuscript, Aug. 2010.
Isner, Jeffrey M., et al. "Excimer Laser Atherectomy", Circulation, Jun. 1990, vol. 81, No. 6, American Heart Association, Dallas, TX, USA.
Israel, Douglas H., et al. "Excimer Laser-Facilitated Balloon Angioplasty of a Nondilateable Lesion", JACC, Oct. 1991, vol. 18, No. 4, American College of Cardiology, New York, USA.
Van Leeuwen, Ton G., et al. "Excimer Laser Induced Bubble: Dimensions, Theory, and Implications for Laser Angioplasty", Lasers in Surgery and Medicine 18, 1996, pp. 381-390, Wiley-Liss Inc., Utrecht, The Netherlands.
Nguyen, H., et al. "Fabrication of multipoint side-firing optical fiber by laser micro-ablation", Optics Letters, May 1, 2017, vol. 42, No. 9, Optical Society of America.
Zheng, W., "Optic Lenses Manufactured on Fiber Ends", 2015, IEEE, Duncan, SC, USA.
Whitesides, George M., et al. "Fluidic Optics", 2006, vol. 6329, SPIE, Cambridge, MA, USA.
Forero, M., et al. "Coronary lithoplasty: a novel treatment for stent underexpansion", Cardiovascular Flashlight, 2018, European Society of Cardiology.
Ghanate, A. D., et al. "Comparative evaluation of spectroscopic models using different multivariate statistical tools in a multicancer scenario", Journal of Biomedical Optics, Feb. 2011, pp. 1-9, vol. 16(2), SPIE.
Roberts, Randy M., et al. "The Energy Partition of Underwater Sparks", The Journal of the Acoustical Society of America, Jun. 1996, pp. 3465-3474, Acoustical Society of America, Austin, TX, USA.
Blackmon, Richard L., et al. "Holmium: YAG Versus Thulium Fiber Laser Lithotripsy", Lasers in Surgery and Medicine, 2010, pp. 232-236, Wiley-Liss Inc.
Varghese, B., "Influence of absorption induced thermal initiation pathway on irradiance threshold for laser induced breakdown", Biomedical Optics Express, 2015, vol. 6, No. 4, Optical Society of America.
Noack, J., "Influence of pulse duration on mechanical effects after laser-induced breakdown in water", Journal of Applied Physics, 1998, pp. 7488-EOA, vol. 83, American Institute of Physics.
Van Leeuwen, Ton G., et al. "Intraluminal Vapor Bubble Induced by Excimer Laser Pulse Causes Microsecond Arterial Dilation and Invagination Leading to Extensive Wall Damage in the Rabbit", Circulation, Apr. 1993, vol. 87, No. 4, American Heart Association, Dallas, TX, USA.
"Custom Medical Skived Tubing", Duke Extrusion, 2025. https://www.dukeextrusion.com/tubing-options/skived-tubing.
Hutchens et al; "Fiber Optic Muzzle Brake Tip for Reducing Fiber Burnback and Stone Retropulsion during Thulium Fiber Laser Lithotripsy," Journal of Biomedical Optics, vol. 22(1): p. 18001, 2017.
Mostafa M. et al., "Use of the Moses Technology to Improve Holmium Laser Lithotripsy Outcomes: A Preclinical Study", Journal Of Endourology, vol. 31, No. 6, Jun. 1, 2017, pp. 598-604, XP093312354.

* cited by examiner 300A
342A
348A
322A
346A 300B
342B
348B
322B
346B 548A
550AF
550AS
552AS
552AF 548D
550DF
550DS
552DF
552DS 548B
550BF
550BS
552BS
552BF 548E
552ES
550EF
550ES
550ET
552EF
552ET 548C
550CF
550CS
552CF
552CS 548F
550FF
550FS
552FF
552FS

LASER PULSE SHAPING TO ENHANCE CONVERSION EFFICIENCY AND PROTECT FIBER OPTIC DELIVERY SYSTEM FOR DISRUPTION OF VASCULAR CALCIUM

RELATED APPLICATION

This application claims priority on U.S. Provisional Application Ser. No. 62/987,060, filed on Mar. 9, 2020. As far as permitted, the contents of U.S. Provisional Application Ser. No. 62/987,060 are incorporated in their entirety herein by reference.

BACKGROUND

Vascular lesions within and adjacent to vessels in the body can be associated with an increased risk for major adverse events, such as myocardial infarction, embolism, deep vein thrombosis, stroke, and the like. Severe vascular lesions can be difficult to treat and achieve patency for a physician in a clinical setting.

Vascular lesions may be treated using interventions such as drug therapy, balloon angioplasty, atherectomy, stent placement, vascular graft bypass, to name a few. Such interventions may not always be ideal or may require subsequent treatment to address the lesion.

Creation of a plasma via optical breakdown of an aqueous solution typically requires a significant amount of energy in a short amount of time upon which it is converted into a therapeutic bubble and/or a therapeutic pressure wave. With sufficiently high energy and short pulse durations, there is potential to damage a distal end of a light guide used to deliver light energy to generate the plasma. A means to enhance the conversion efficiency of the light energy to (plasma) pressure wave and bubble growth would reduce the required power handling requirements of the optical delivery system. Therefore, less input energy would be required for an equivalent therapy while minimizing potential damage to the light guide.

Creation of the plasma near the distal end of a small diameter light guide as in the case of aqueous optical breakdown as one method for an intravascular lithotripsy catheter has the potential for self-damage due to its proximity to the plasma creation and/or the pressure wave, high plasma temperatures, and waterjet from collapse of the bubble, as non-exclusive examples.

SUMMARY

The present invention is directed toward a catheter system for placement within a blood vessel having a vessel wall. The catheter system can be used for treating a treatment site within or adjacent to the vessel wall. In various embodiments, the catheter system includes a power source, a controller, and a light guide. The power source generates a plurality of energy pulses. The controller controls the power source so that the plurality of energy pulses cooperate to produce a composite energy pulse having a composite pulse shape. The light guide receives the composite energy pulse. The light guide emits light energy in a direction away from the light guide to generate a plasma pulse away from the light guide.

In some embodiments, the power source is a laser.

In certain embodiments, the light guide is an optical fiber.

In some embodiments, the catheter system further includes an inflatable balloon that encircles a distal end of the light guide.

In certain embodiments, each of the plurality of energy pulses are sub-millisecond pulses.

In some embodiments, each of the energy pulses has a pulse width, and the energy pulses are added to one another so that the composite energy pulse has a pulse width that is longer than the pulse width of any one of the energy pulses.

In certain embodiments, at least two of the plurality of energy pulses have the same wavelength as one another.

In some embodiments, at least one of the plurality of energy pulses has a wavelength that is different from the other energy pulses.

In certain embodiments, at least two of the plurality of energy pulses have pulse widths that are the same as one another.

In some embodiments, at least two of the plurality of energy pulses have pulse widths that are different from one another.

In certain embodiments, at least two of the plurality of energy pulses have light energy that is the same as one another.

In some embodiments, at least two of the plurality of energy pulses have light energy is different from one another.

In various embodiments, the plurality of energy pulses combine to generate one continuous plasma pulse away from the distal end of the light guide.

In certain embodiments, the composite energy pulse has a pulse amplitude that increases over time.

In some embodiments, the composite energy pulse has a pulse amplitude that decreases over time.

In certain embodiments, the composite energy pulse has a pulse width having a time t, the composite energy pulse having a temporal peak that occurs after time t/2.

In various embodiments, the composite energy pulse has a pulse width having a time t, the composite energy pulse having a temporal peak that occurs before time t/2.

In certain embodiments, the composite energy pulse has a pulse width having a time t, the composite energy pulse having a temporal peak that occurs approximate at time t/2.

In some embodiments, the composite energy pulse has a temporal peak that remains substantially constant over time.

In certain embodiments, the composite energy pulse generates a plurality of plasma pulses away from the distal end of the light guide. In some such embodiments, the plurality of plasma pulses are generated at different times from one another.

In some embodiments, the composite energy pulse includes two temporal peaks that are substantially similar to one another. Still further, or in the alternative, in certain embodiments, the composite energy pulse includes two temporal peaks that are different from one another.

In certain embodiments, the composite energy pulse has a pulse amplitude that generally increases over time. In other embodiments, the composite energy pulse has a pulse amplitude that generally decreases over time.

In some embodiments, the composite energy pulse has a pulse width having a time t, the composite energy pulse having a temporal peak that occurs after time t/2. Alternatively, in other embodiments, the composite energy pulse has a pulse width having a time t, the composite energy pulse having a temporal peak that occurs before time t/2. Still alternatively, in still other embodiments, the composite energy pulse has a pulse width having a time t, the composite energy pulse having a temporal peak that occurs approximately at time t/2. Further, in some such embodiments, the composite energy pulse has a temporal peak that remains substantially constant over time.

In certain embodiments, the light guide has a distal end, and the catheter system is configured to generate a pre-bubble at a distal end of the light guide. In some such embodiments, the composite energy pulse is configured to generate the pre-bubble at a distal end of the light guide. In one such embodiment, the pre-bubble is generated by electrolysis. In another such embodiment, the pre-bubble is generated by using a resistive heater. In still another such embodiment, the pre-bubble is generated with a fluid that is delivered to near the distal end of the light guide.

In some embodiments, the controller can control a timing of the composite energy pulse relative to a start of the generation of the pre-bubble. For example, in certain such embodiments, the composite energy pulse is generated greater than approximately 1 ns and less than approximately 100 ms after a start of the generation of the pre-bubble. In other such embodiments, the composite energy pulse is generated greater than approximately 100 ns and less than approximately 1 ms after a start of the generation of the pre-bubble. In still other such embodiments, the composite energy pulse is generated greater than approximately 1 μs and less than approximately 10 ms after a start of the generation of the pre-bubble. In yet other such embodiments, the composite energy pulse is generated greater than approximately 5 μs and less than approximately 500 μs after a start of the generation of the pre-bubble. In still yet other such embodiments, the composite energy pulse is generated approximately 50 μs after a start of the generation of the pre-bubble.

In certain embodiments, the power source includes (i) a seed source, and (ii) an amplifier, the seed source emitting a low-power seed pulse, the amplifier being in optical communication with the seed source, the amplifier increasing the power of the seed pulse to generate an energy pulse.

In some embodiments, the power source includes (i) a plurality of seed sources, and (ii) a plurality of amplifiers, the seed sources each emitting a low-power seed pulse, the plurality of amplifiers each being in optical communication with one of the seed sources and each receiving one of the low-power seed pulses, each amplifier increasing the power of the seed pulse that is received by the respective amplifier, the plurality of amplifiers generating the plurality of energy pulses.

In certain embodiments, the power source includes (i) a plurality of seed sources, and (ii) an amplifier, the seed sources each emitting a low-power seed pulse, the amplifier being in optical communication with each of the seed sources and receiving the low-power seed pulses, the amplifier increasing the power of each of the seed pulses that is received by the amplifier, the amplifier generating the plurality of energy pulses.

In various embodiments, the catheter system further includes a hydrophobic material that is positioned near a distal end of the light guide.

In certain embodiments, the catheter system further includes a hydrophobic material that is positioned on a distal end of the light guide.

In some embodiments, the catheter system further includes a nano surface that is positioned near a distal end of the light guide.

In certain embodiments, the catheter system further includes a nano surface that is positioned on a distal end of the light guide.

In some embodiments, the nano surface is textured.

In certain applications, the present invention is also directed toward a method for treating a treatment site within or adjacent to a vessel wall, the method including the steps of: generating a plurality of energy pulses with a power source; controlling the power source with a controller so that the plurality of energy pulses cooperate to produce a composite energy pulse that is sent to a light guide, the composite energy pulse having a composite pulse shape; producing light energy that is emitted from the light guide with the composite energy pulse that is sent to the light guide; and generating a plasma pulse from the light energy away from the light guide.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

Figure 1:
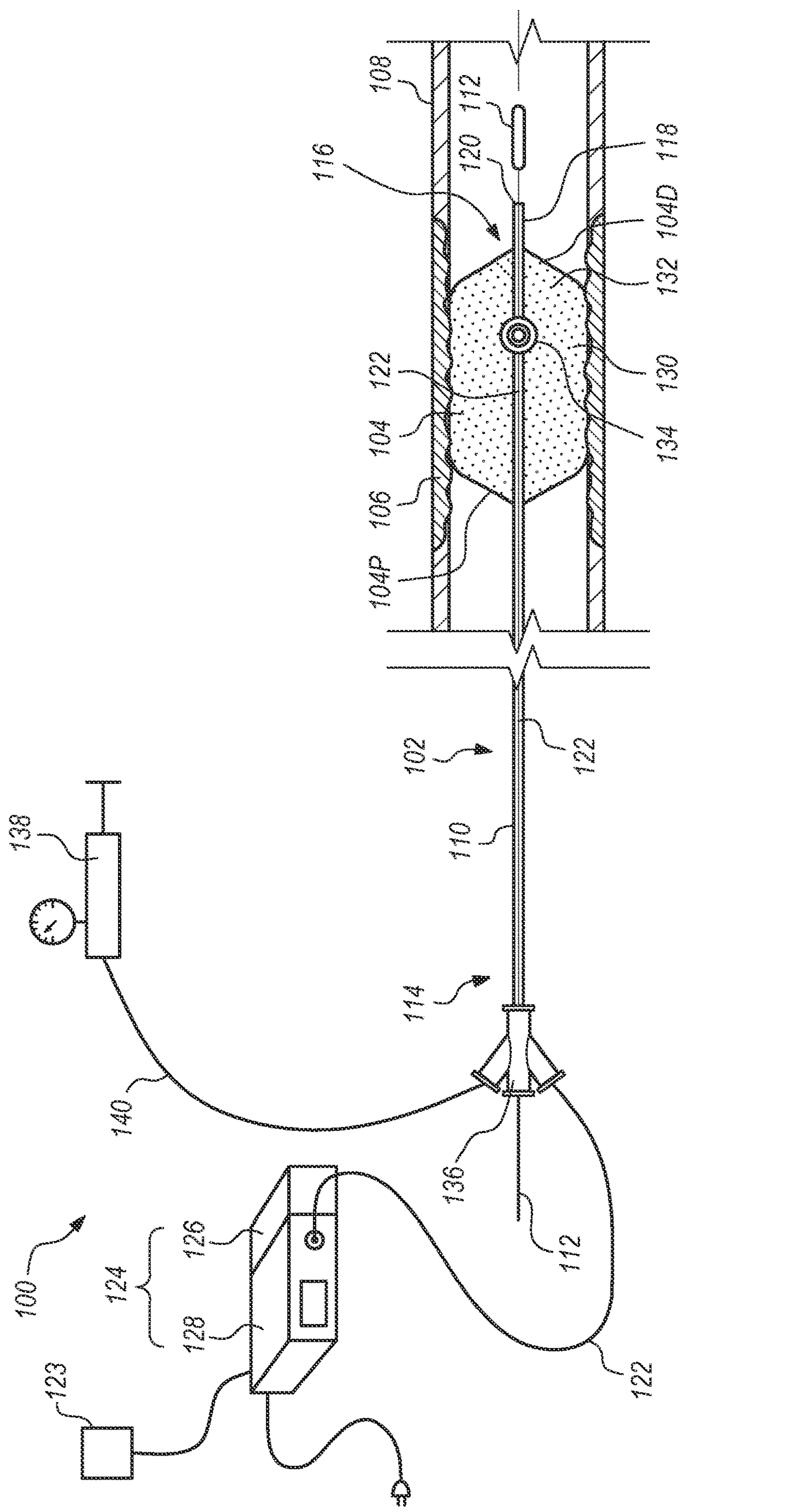
FIG. 1 is a schematic cross-sectional view of a catheter system having features of the present invention in accordance with various embodiments herein.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DESCRIPTION

Treatment of vascular lesions can reduce major adverse events or death in affected subjects. As referred to herein, a major adverse event is one that can occur anywhere within the body due to the presence of a vascular lesion (also sometime referred to herein as a "treatment site"). Major adverse events can include, but are not limited to, major adverse cardiac events, major adverse events in the peripheral or central vasculature, major adverse events in the brain, major adverse events in the musculature, or major adverse events in any of the internal organs.

As used herein, the treatment site can include a vascular lesion such as a calcified vascular lesion or a fibrous vascular lesion (hereinafter sometimes referred to simply as a "lesion" or "treatment site"), typically found in a blood vessel and/or a heart valve. Plasma formation can initiate a pressure wave and can initiate the rapid formation of one or more bubbles that can rapidly expand to a maximum size and then dissipate through a cavitation event that can also launch a pressure wave upon collapse. The rapid expansion of the plasma-induced bubbles can generate one or more pressure waves within a balloon fluid and thereby impart pressure waves upon the treatment site. The pressure waves can transfer mechanical energy through an incompressible balloon fluid to a treatment site to impart a fracture force on the lesion. Without wishing to be bound by any particular theory, it is believed that the rapid change in balloon fluid momentum upon a balloon wall of the inflatable balloon that is in contact with or positioned near the lesion is transferred to the lesion to induce fractures in the lesion.

Those of ordinary skill in the art will realize that the following detailed description of the present invention is illustrative only and is not intended to be in any way limiting. Other embodiments of the present invention will readily suggest themselves to such skilled persons having the benefit of this disclosure. Additionally, other methods of delivering energy to the lesion can be utilized, including, but not limited to, electric current induced plasma generation.

Reference will now be made in detail to implementations of the present invention as illustrated in the accompanying drawings.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it is appreciated that such a development effort might be complex and time-consuming, but would nevertheless be a routine undertaking of engineering for those of ordinary skill in the art having the benefit of this disclosure.

As used herein, the terms "intravascular lesion", "vascular lesion" and "treatment site" are used interchangeably unless otherwise noted. As such, the intravascular lesions and/or the vascular lesions are sometimes referred to herein simply as "lesions" and can include lesions located at or near blood vessels or heart valves.

It is appreciated that the catheter systems herein can include many different forms and/or configurations other than those specifically shown and/or described herein. Referring now to FIG. 1, a schematic cross-sectional view is shown of a catheter system in accordance with various embodiments herein. A catheter system 100 is suitable for imparting pressure to induce fractures in a treatment site within or adjacent a vessel wall of a blood vessel and/or a heart valve. In the embodiment illustrated in FIG. 1, the catheter system 100 can include one or more of a catheter 102, one or more light guides 122, a controller 123, a power source 124, a manifold 136 and a fluid pump 138.

The catheter 102 includes an inflatable balloon 104 (sometimes referred to herein as "balloon"). The catheter 102 is configured to move to a treatment site 106 within or adjacent to a blood vessel 108. The treatment site 106 can include a treatment site such as a calcified vascular lesion, for example. Additionally, or in the alternative, the treatment site 106 can include a vascular lesion such as a fibrous vascular lesion.

The catheter 102 can include the balloon 104, a catheter shaft 110 and a guidewire 112. The balloon can be coupled to the catheter shaft 110. The balloon can include a balloon proximal end 104P and a balloon distal end 104D. The catheter shaft 110 can extend between a shaft proximal end 114 and a shaft distal end 116. The catheter shaft 110 can include a guidewire lumen 118 which is configured to move over the guidewire 112. The catheter shaft 110 can also include an inflation lumen (not shown). In some embodiments, the catheter 102 can have a distal end opening 120 and can accommodate and be moved over and/or along the guidewire 112 so that the balloon 104 is positioned at or near the treatment site 106.

The catheter shaft 110 of the catheter 102 can encircle one or more light guides 122 (only one light guide 122 is illustrated in FIG. 1 for clarity) in optical communication with a power source 124. The light guide 122 can be at least partially disposed along and/or within the catheter shaft 110 and at least partially within the balloon 104. In various embodiments, the light guide 122 can be an optical fiber and the power source 124 can be a laser. The power source 124 can be in optical communication with the light guide 122. In some embodiments, the catheter shaft 110 can encircle multiple light guides such as a second light guide, a third light guide, etc.

The balloon 104 can include a balloon wall 130. The balloon 104 can expand from a collapsed configuration suitable for advancing at least a portion of the catheter shaft 102 through a patient's vasculature to an expanded configuration suitable for anchoring the catheter 102 into position relative to the treatment site 106.

The controller 123 can control the power source 124 so that the power source can generate one or more energy pulses 242A, 242B, 342A, 342B (illustrated in FIGS. 2A-3B, for example) as provided in greater detail herein. The controller 123 may also perform other relevant functions to control operation of the catheter 102.

The power source 124 of the catheter system 100 can be configured to provide one or more sub-millisecond energy pulses that are received by the light guide 122. As provided in greater detail herein, in various embodiments, the energy pulses can combine or otherwise cooperate to produce a composite energy pulse having a composite pulse shape (not shown in FIG. 1) that is then received by the light guide 122. The light guide 122 acts as a conduit for light energy that is generated by the composite energy pulse. In certain embodiments, the power source 124 can include one or more seed sources 126 and one or more amplifiers 128. Each amplifier 128 can be in optical communication with at least one of the seed sources 126. The seed source(s) 126 can each emit a low-power seed pulse. The amplifier 128 can increase the power of the seed pulse to generate the energy pulse. In one embodiment, the power source can include one seed source 126 and one amplifier 128. Alternatively, the power source 124 can include a plurality of seed sources 126 and one amplifier 128. Still alternatively, the power source 124 can include a plurality of seed sources 126 and a plurality of amplifiers 128.

The light energy that is generated by the composite energy pulse is delivered by the light guide 122 to a location within the balloon 104. The light energy induces plasma formation in the form of a plasma pulse 134 that occurs in the balloon fluid 132 within the balloon 104. The plasma pulse 134 causes rapid bubble formation, and imparts pressure waves upon the treatment site 106. Exemplary plasma pulses 134 are shown in FIG. 1. The balloon fluid 132 can be a liquid or a gas. As provided in greater detail herein, the plasma-induced bubbles 134 are intentionally formed at some distance away from the light guide 122 so that the likelihood of damage to the light guide is decreased.

In various embodiments, the sub-millisecond pulses of light can be delivered to near the treatment site 106 at a frequency of from at least approximately 1 hertz (Hz) up to approximately 5000 Hz. In some embodiments, the sub-millisecond pulses of light can be delivered to near the treatment site 106 at a frequency from at least 30 Hz to 1000 Hz. In other embodiments, the sub-millisecond pulses of light can be delivered to near the treatment site 106 at a frequency from at least 10 Hz to 100 Hz. In yet other embodiments, the sub-millisecond pulses of light can be delivered to near the treatment site 106 at a frequency from at least 1 Hz to 30 Hz. In some embodiments, the sub-millisecond pulses of light can be delivered to near the treatment site 106 at a frequency that can be greater than or equal to 1 Hz, 2 Hz, 3 Hz, 4 Hz, 5 Hz, 6 Hz, 7 Hz, 8 Hz, or 9 Hz, 10 Hz, 20 Hz, 30 Hz, 40 Hz, 50 Hz, 60 Hz, 70 Hz, 80 Hz, 90 Hz, 100 Hz, 200 Hz, 300 Hz, 400 Hz, 500 Hz, 600 Hz, 700 Hz, 800 Hz, 900 Hz, 1000 Hz, 1250 Hz, 1500 Hz, 1750 Hz, 2000 Hz, 2250 Hz, 2500 Hz, 2750 Hz, 3000 Hz, 3250 Hz, 3500 Hz, 3750 Hz, 4000 Hz, 4250 Hz, 4500 Hz, 4750 Hz, or 5000 Hz or can be an amount falling within a range between any of the foregoing. Alternatively, the sub-millisecond pulses of light can be delivered to near the treatment site 106 at a frequency that can be greater than 5000 Hz.

It is appreciated that the catheter system 100 herein can include any number of light guides 122 in optical communication with the power source 124 at the proximal portion 114, and with the balloon fluid 132 within the balloon 104 at the distal portion 116. For example, in some embodiments, the catheter system 100 herein can include from one light guide 122 to five light guides 122. In other embodiments, the catheter system 100 herein can include from five light guides to fifteen light guides. In yet other embodiments, the catheter system 100 herein can include from ten light guides to thirty light guides. The catheter system 100 herein can include 1-30 light guides. It is appreciated that the catheter system 100 herein can include any number of light guides that can fall within a range, wherein any of the forgoing numbers can serve as the lower or upper bound of the range, provided that the lower bound of the range is a value less than the upper bound of the range. In some embodiments, the catheter system 100 herein can include greater than 30 light guides.

The manifold 136 can be positioned at or near the shaft proximal end 114. The manifold 136 can include one or more proximal end openings that can receive the one or more light guides, such as light guide 122, the guidewire 112, and/or an inflation conduit 140. The catheter system 100 can also include the fluid pump 138 that is configured to inflate the balloon 104 with the balloon fluid 132 and/or deflate the balloon 104 as needed.

As with all embodiments illustrated and described herein, various structures may be omitted from the figures for clarity and ease of understanding. Further, the figures may include certain structures that can be omitted without deviating from the intent and scope of the invention.

Figure 2A:
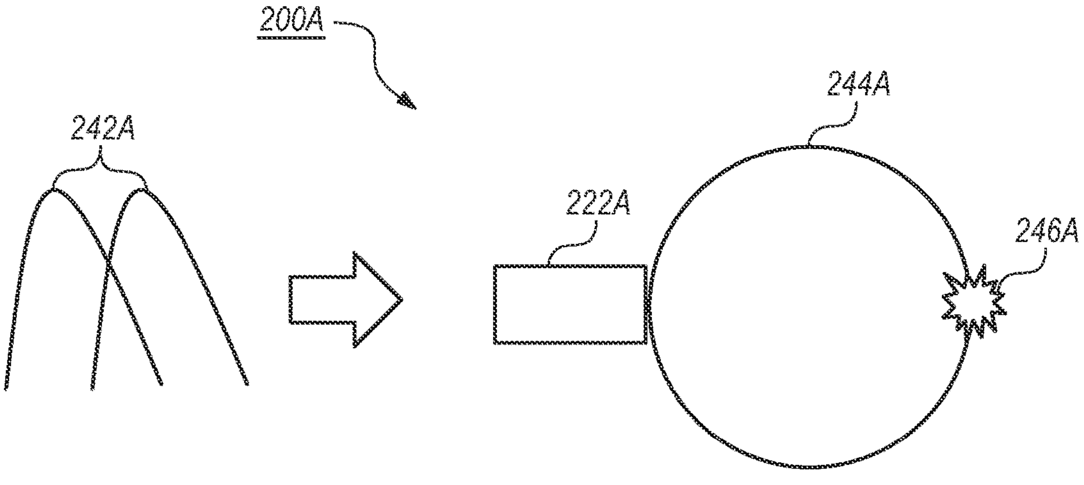
FIG. 2A is a simplified schematic diagram illustrating a first embodiment of a portion of the catheter system that generates a plurality of overlapping energy pulses that are sent to a light guide to generate a plasma pulse.

FIG. 2A is a simplified schematic diagram illustrating a first embodiment of a portion of the catheter system 200A that generates a plurality of overlapping energy pulses 242A. In this embodiment, the overlapping energy pulses 242A combine and are sent to a light guide 222A to generate a pre-bubble 244A and a plasma pulse 246A. The plasma pulse 246A generates pressure waves (not shown), which then disrupt the calcified lesion at or near the treatment site 106 (illustrated in FIG. 1). By combining a plurality of energy pulses 242A in a structured manner, a composite energy pulse 348A (illustrated in FIG. 3A, for example) is generated. As provided in greater detail below, in this and other embodiments, the composite energy pulse 348A can be customized or otherwise tailored to achieve a specific pre-bubble 244A and/or plasma pulse 246A.

In one embodiment, and in the embodiments which follow, the energy pulses 242A can be substantially similar in shape, amplitude and/or pulse width (duration). Alternatively, one or more of the shape, amplitude and/or duration pulse width can be different from energy pulse 242A to energy pulse 242A. With this design, the composite energy pulse can be customized in a manner that is advantageous to generating one or more plasma pulses 246A having the desired characteristics.

Figure 2B:
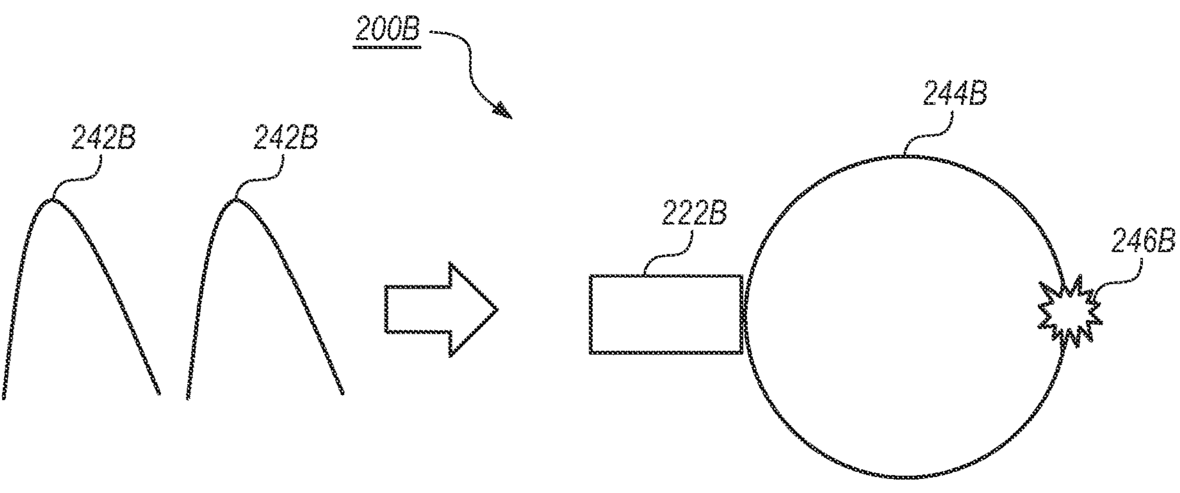
FIG. 2B is a simplified schematic diagram illustrating another embodiment of a portion of the catheter system that generates a plurality of non-overlapping energy pulses that are sent to the light guide to generate the plasma pulse.

FIG. 2B is a simplified schematic diagram illustrating a first embodiment of a portion of the catheter system 200B that generates a plurality of separate, spaced apart energy pulses 242B. In this embodiment, the spaced apart energy pulses 242B are sent to a light guide 222B to generate a pre-bubble 244B and/or a plasma pulse 246B. The plasma pulse 246B generates pressure waves (not shown), which then disrupt the calcified lesion at or near the treatment site 106 (illustrated in FIG. 1). By using a plurality of energy pulses 242B in a structured manner, a composite energy pulse 348B (illustrated in FIG. 3B, for example) is generated. As provided in greater detail below, in this and other embodiments, the composite energy pulse 348B can be customized or otherwise tailored to achieve a specific pre-bubble 244B and/or plasma pulse 246B.

Figures 3A, 3B:
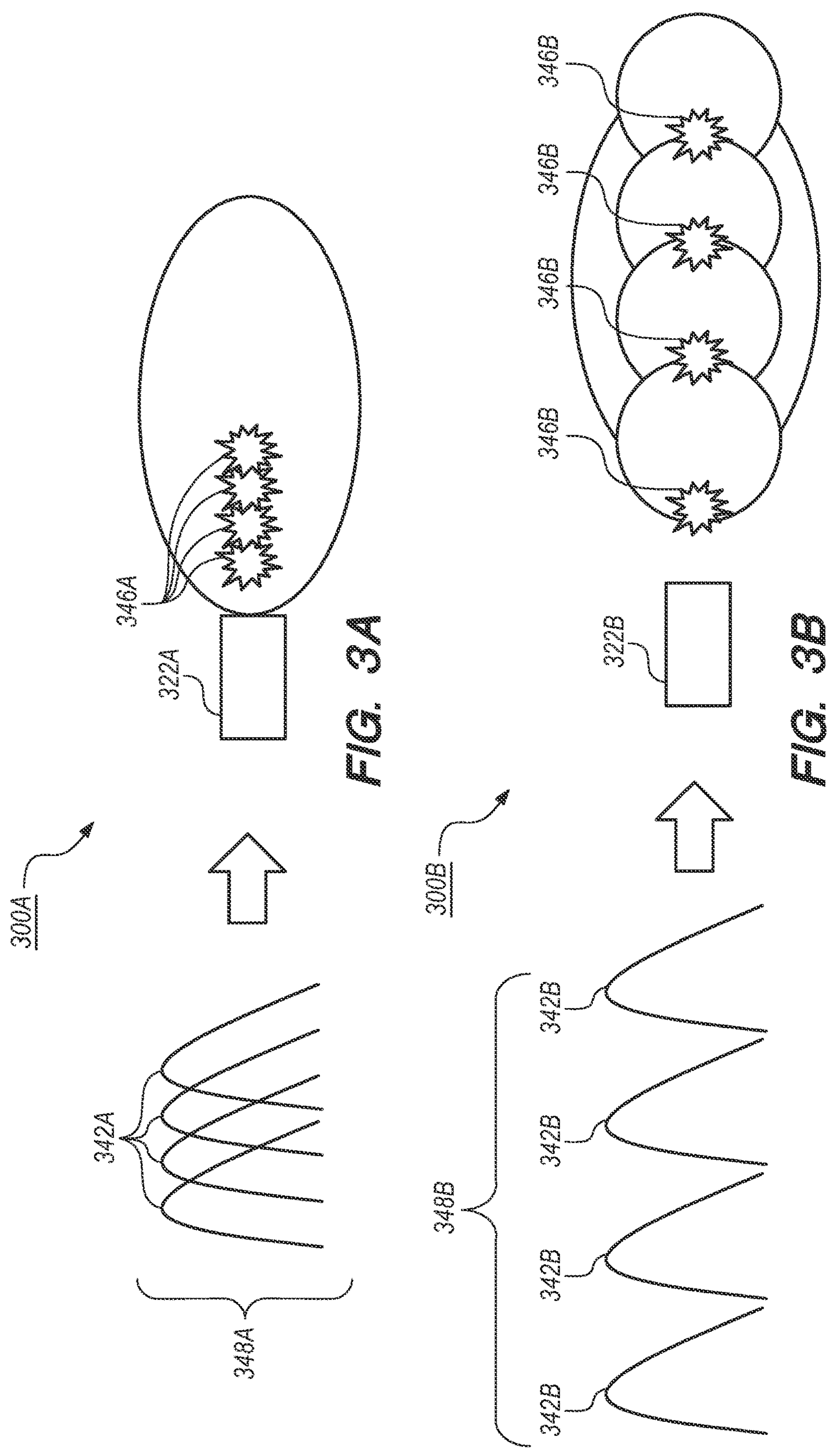
FIG. 3A is a simplified schematic diagram illustrating an embodiment of a portion of the catheter system that generates a plurality of overlapping energy pulses that are sent to the light guide to generate the plurality of plasma pulses.
FIG. 3B is a simplified schematic diagram illustrating another embodiment of a portion of the catheter system that generates a plurality of non-overlapping energy pulses that are sent to the light guide to generate the plasma pulse.

FIG. 3A is a simplified schematic diagram illustrating an embodiment of a portion of the catheter system 300A that generates a plurality of overlapping energy pulses 342A to produce a composite energy pulse 348A. The composite energy pulse 348A is sent to the light guide 322A and can generate one or more plasma pulses 346A. In this embodiment, the plasma pulses 346A can occur in relatively close proximity to one another and/or close in time to one another. In the embodiment illustrated in FIG. 3A, the plasma pulses 346A occur essentially continuously, e.g. the plasma pulses 346A are substantially in rapid-fire succession to basically create one continuous plasma pulse 346A having a longer duration than any one single plasma pulse 346A. The plasma pulses 346A can generate pressure waves (not shown), which then disrupt the calcified lesion at or near the treatment site 106 (illustrated in FIG. 1).

In one embodiment, and in the embodiments which follow, the energy pulses 342A can be substantially similar in shape, amplitude and/or pulse width (duration). Alternatively, one or more of the shape, amplitude and/or duration pulse width can be different from energy pulse 342A to energy pulse 342A.

FIG. 3B is a simplified schematic diagram illustrating an embodiment of a portion of the catheter system 300B that generates a plurality of separate, spaced apart energy pulses 342B to produce a composite energy pulse 348B. The composite energy pulse 348B is sent to the light guide 322B and can generate one or more plasma pulses 346B. In this embodiment, the plasma pulses 346B can have a greater distance between one another and/or a greater time between each plasma pulse 346B. The plasma pulses 346B can generate pressure waves (not shown), which then disrupt the calcified lesion at or near the treatment site 106 (illustrated in FIG. 1).

Figure 4A:
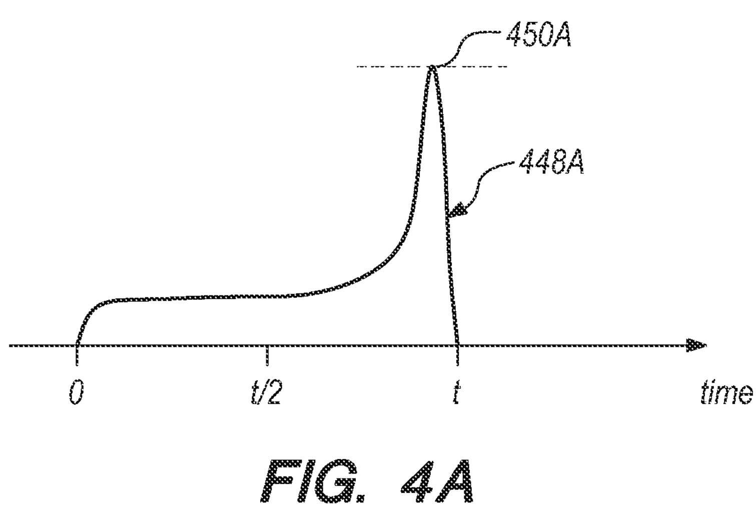
FIG. 4A is a simplified graph illustrating one embodiment of a composite energy pulse having a composite pulse shape.

FIG. 4A is a simplified graph illustrating one embodiment of a composite energy pulse 448A having a pulse width with a duration of t. In this embodiment, the composite energy pulse 448A was formed by combining a plurality of energy pulses (illustrated in FIGS. 2A-2B and FIGS. 3A-3B, for example), as set forth in greater detail herein. In the embodiment illustrated in FIG. 4A, the composite energy pulse 448A has a temporal peak 450A (greatest amplitude) that occurs after time t/2. Further, in this embodiment, the composite energy pulse 448A has relatively low energy at the onset, which creates pre-seeding prior to the plasma pulse (not shown in FIG. 4A). In this embodiment, the composite energy pulse 448A has a greater energy toward the end of the pulse, which ultimately generates the plasma pulse.

Figure 4B:
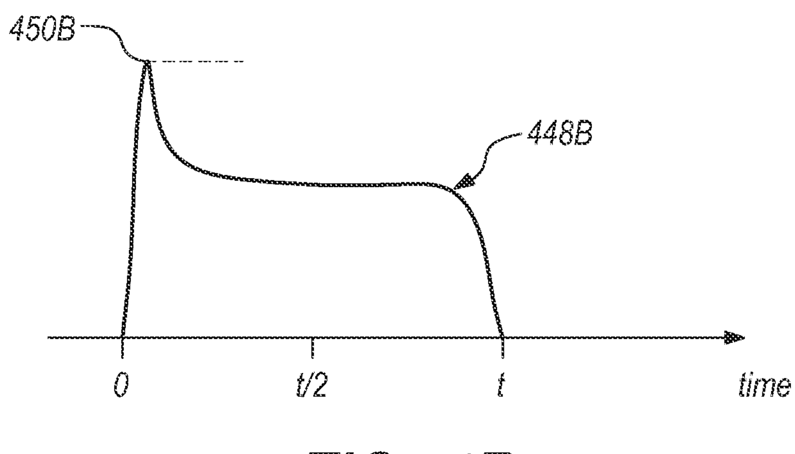
FIG. 4B is a simplified graph illustrating another embodiment of the composite energy pulse having another composite pulse shape.

FIG. 4B is a simplified graph illustrating one embodiment of a composite energy pulse 448B having a pulse width with a duration of t. In this embodiment, the composite energy pulse 448B was formed by combining a plurality of energy pulses (illustrated in FIGS. 2A-2B and FIGS. 3A-3B, for example), as set forth in greater detail herein. In the embodiment illustrated in FIG. 4B, the composite energy pulse 448B has a temporal peak 450B (greatest amplitude) that occurs before time t/2, resulting in the plasma pulse (not shown in FIG. 4B). Further, in this embodiment, the composite energy pulse 448B maintains a relatively high, sustaining energy after the temporal peak 450B, which can feed the plasma pulse with a relatively high energy long tail after the temporal peak 450B.

Figure 4C:
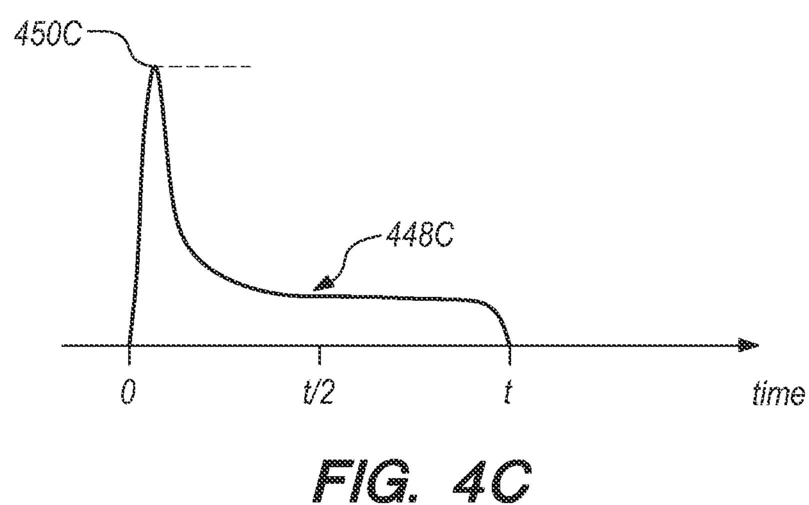
FIG. 4C is a simplified graph illustrating yet another embodiment of the composite energy pulse having another composite pulse shape.

FIG. 4C is a simplified graph illustrating one embodiment of a composite energy pulse 448C having a pulse width with a duration of t. In this embodiment, the composite energy pulse 448C was formed by combining a plurality of energy pulses (illustrated in FIGS. 2A-2B and FIGS. 3A-3B, for example), as set forth in greater detail herein. In the embodiment illustrated in FIG. 4C, the composite energy pulse 448C has a temporal peak 450C (greatest amplitude) that occurs before time t/2, resulting in the plasma pulse (not shown in FIG. 4C). Further, in this embodiment, the composite energy pulse 448C maintains a relatively low, sustaining energy after the temporal peak 450C, which can feed the plasma pulse with a relatively low energy long tail after the temporal peak 450C.

FIGS. 5A-5F illustrate non-exclusive embodiments of certain representative composite energy pulses that can be generated using the devices and methods provided herein. It is understood that these embodiments are not intended to illustrate all possible composite energy pulses, as doing so would be impossible. Rather, FIGS. 5A-5F are provided to illustrate that any composite energy pulse shape is possible using the devices and methods disclosed herein.

Figures 5A, 5B, 5C, 5D, 5E, 5F:
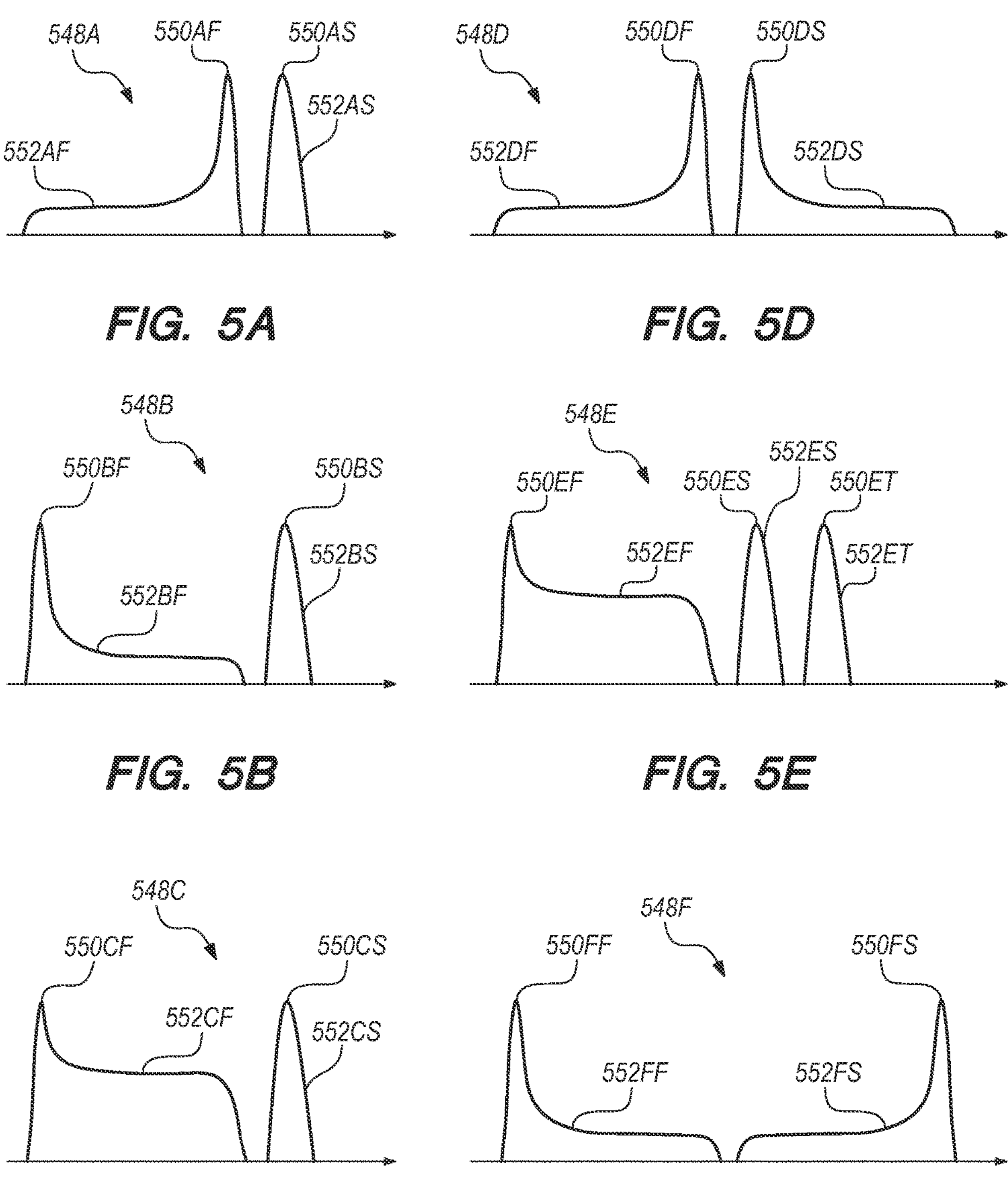
FIG. 5A is a simplified graph illustrating an embodiment of the composite energy pulse having another composite pulse shape.
FIG. 5B is a simplified graph illustrating another embodiment of the composite energy pulse having another composite pulse shape.
FIG. 5C is a simplified graph illustrating yet another embodiment of the composite energy pulse having another composite pulse shape.
FIG. 5D is a simplified graph illustrating still another embodiment of the composite energy pulse having another composite pulse shape.
FIG. 5E is a simplified graph illustrating another embodiment of the composite energy pulse having another composite pulse shape.
FIG. 5F is a simplified graph illustrating but another embodiment of the composite energy pulse having another composite pulse shape.

FIG. 5A is a simplified graph illustrating an embodiment of the composite energy pulse 548A having one composite pulse shape. In this embodiment, the composite energy pulse 548A includes two (or more) spaced apart temporal peaks such as a first temporal peak 550AF and a second temporal peak 550AS. Further, in one embodiment, the composite energy pulse 548A can have two (or more) separate, spaced apart pulses including a first pulse 552AF and a second pulse 552AS, each having a different pulse shape from one another, although it is understood that the pulse shapes can alternatively be substantially similar or identical to one another.

FIG. 5B is a simplified graph illustrating an embodiment of the composite energy pulse 548B having one composite pulse shape. In this embodiment, the composite energy pulse 548B includes two (or more) spaced apart temporal peaks such as a first temporal peak 550BF and a second temporal peak 550BS. Further, in one embodiment, the composite energy pulse 548B can have two (or more) separate, spaced apart pulses including a first pulse 552BF and a second pulse 552BS, each having a different pulse shape from one another, although it is understood that the pulse shapes can alternatively be substantially similar or identical to one another.

FIG. 5C is a simplified graph illustrating an embodiment of the composite energy pulse 548C having one composite pulse shape. In this embodiment, the composite energy pulse 548C includes two (or more) spaced apart temporal peaks such as a first temporal peak 550CF and a second temporal peak 550CS. Further, in one embodiment, the composite energy pulse 548C can have two (or more) separate, spaced apart pulses including a first pulse 552CF and a second pulse 552CS, each having a different pulse shape from one another, although it is understood that the pulse shapes can alternatively be substantially similar or identical to one another.

FIG. 5D is a simplified graph illustrating an embodiment of the composite energy pulse 548D having one composite pulse shape. In this embodiment, the composite energy pulse 548D includes two (or more) spaced apart temporal peaks such as a first temporal peak 550DF and a second temporal peak 550DS. Further, in one embodiment, the composite energy pulse 548D can have two (or more) separate, spaced apart pulses including a first pulse 552DF and a second pulse 552DS, each having a different pulse shape from one another, although it is understood that the pulse shapes can alternatively be substantially similar or identical to one another.

FIG. 5E is a simplified graph illustrating an embodiment of the composite energy pulse 548E having one composite pulse shape. In this embodiment, the composite energy pulse 548E includes three (or more) spaced apart temporal peaks such as a first temporal peak 550EF, a second temporal peak 550ES and a third temporal peak 550ET. Further, in one embodiment, the composite energy pulse 548E can have three (or more) separate, spaced apart pulses including a first pulse 552EF, a second pulse 552ES and a third pulse 552ET, so that at least two of the pulses 552EF, 552ES have different pulse shapes from one another, although it is understood that the pulse shapes can alternatively all be substantially similar or identical to one another, or still alternatively, can be all different from one another.

FIG. 5F is a simplified graph illustrating an embodiment of the composite energy pulse 548F having one composite pulse shape. In this embodiment, the composite energy pulse 548F includes two (or more) spaced apart temporal peaks such as a first temporal peak 550FF and a second temporal peak 550FS. Further, in one embodiment, the composite energy pulse 548F can have two (or more) separate, spaced apart pulses including a first pulse 552FF and a second pulse 552FS, each having a different pulse shape from one another, although it is understood that the pulse shapes can alternatively be substantially similar or identical to one another.

Figures 6A, 6B, 6C, 6D:
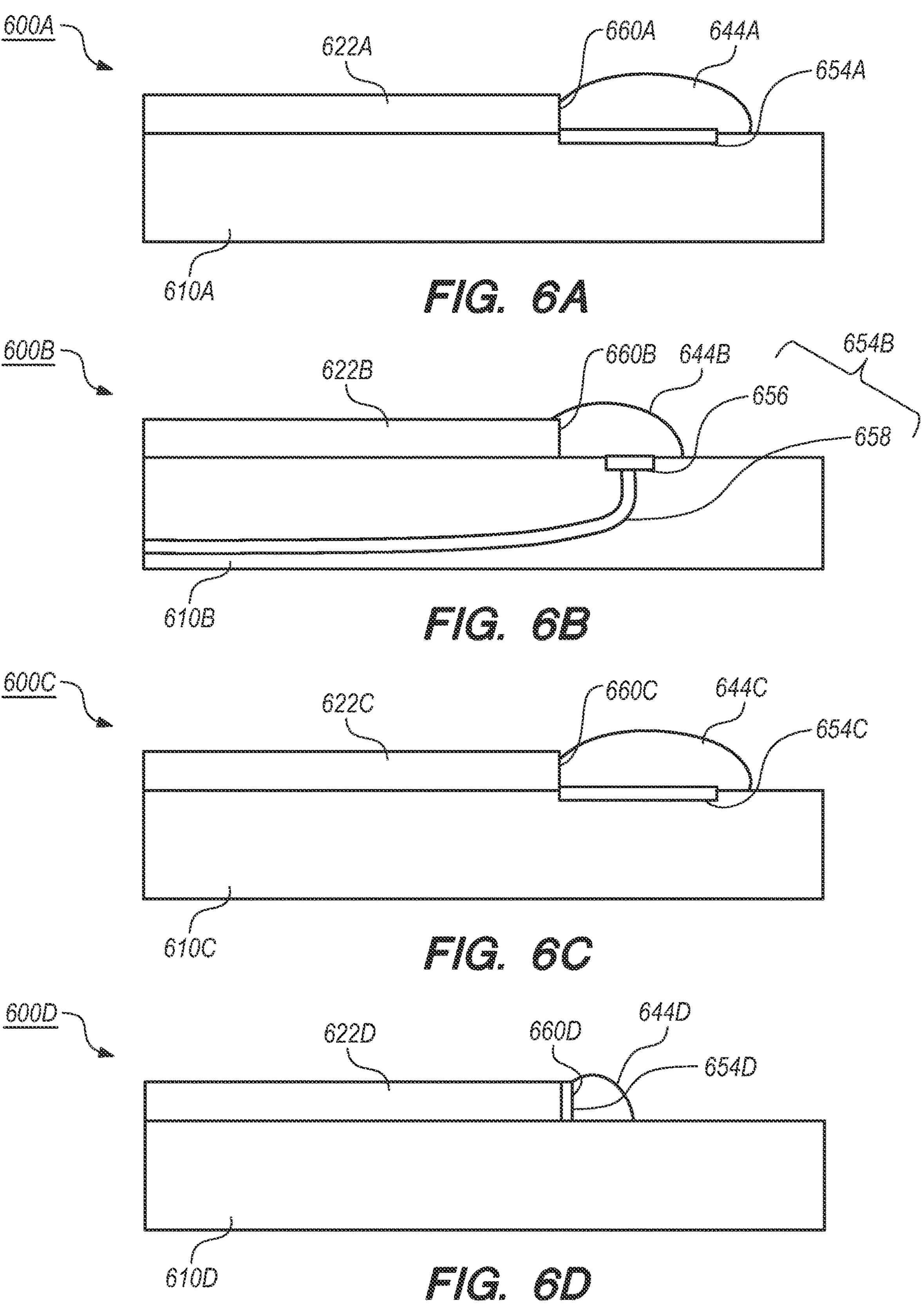
FIG. 6A is a simplified schematic diagram illustrating an embodiment of a portion of the catheter system that generates a pre-bubble.
FIG. 6B is a simplified schematic diagram illustrating another embodiment of a portion of the catheter system that generates the pre-bubble.
FIG. 6C is a simplified schematic diagram illustrating yet another embodiment of a portion of the catheter system that generates the pre-bubble.
FIG. 6D is a simplified schematic diagram illustrating still another embodiment of a portion of the catheter system that generates the pre-bubble.

FIG. 6A is a simplified schematic diagram illustrating an embodiment of a portion of the catheter system 600A that generates a pre-bubble 644A. In this embodiment, the catheter system 600A includes a catheter shaft 610A, a light guide 622A and a pre-bubble generator 654A. The pre-bubble generator 654A generates the pre-bubble 644A to provide a gap between the light guide 622A and a plasma pulse (not shown in FIG. 6A) that will ultimately be generated. In one such embodiment, the pre-bubble generator 654A can include a resistive heater. Alternatively, or in addition, the pre-bubble generator 654A can include a pair (or more) of electrolysis electrodes or any other material that would encourage or promote generation of a pre-bubble 644A at or near a distal end 660A of the light guide 622A. With these designs, damage to the light guide 622A is inhibited because the plasma pulse does not occur immediately at or on the light guide 622A, but instead occurs away from the light guide 622A.

FIG. 6B is a simplified schematic diagram illustrating another embodiment of a portion of the catheter system 600B that generates the pre-bubble 644B. In this embodiment, the catheter system 600B includes a catheter shaft 610B, a light guide 622B and a pre-bubble generator 654B. The pre-bubble generator 654B generates the pre-bubble 644B to provide a gap between the light guide 622B and a plasma pulse (not shown in FIG. 6B) that will ultimately be generated. In one such embodiment, the pre-bubble generator 654B can include a fluid port 656 and a fluid line 658 that is in fluid communication with the fluid port 656. In this embodiment, a fluid (such as air, in one non-exclusive embodiment) can be delivered to the fluid port 656 via the fluid line 658, which can generate the pre-bubble 644B. With this design, damage to the light guide 622B is inhibited because the plasma pulse does not occur immediately at the distal end 660B or anywhere on the light guide 622B, but instead occurs away from the light guide 622B.

FIG. 6C is a simplified schematic diagram illustrating yet another embodiment of a portion of the catheter system 600C that generates the pre-bubble 644C. In this embodiment, the catheter system 600C includes a catheter shaft 610C, a light guide 622C and a pre-bubble generator 654C. The pre-bubble generator 654C generates the pre-bubble 644C to provide a gap between the light guide 622C and a plasma pulse (not shown in FIG. 6C) that will ultimately be generated. In one such embodiment, the pre-bubble generator 654C can include a hydrophobic coating. In this embodiment, surface tension is created so that the pre-bubble would self-form due to hydrophobicity forces. Alternatively, or in addition, the pre-bubble generator 654C can include a nano-textured surface or any other surface or material that would encourage or promote generation of a pre-bubble at or near a distal end 660C of the light guide 622C. In this embodiment, the pre-bubble generator 654C is positioned on the catheter shaft 610C. However, it is recognized that the pre-bubble generator 654C can be positioned at or on another structure within the catheter system 600C. With this design, damage to the light guide 622C is inhibited because the plasma pulse does not occur immediately at or on the light guide 622C, but instead occurs away from the light guide 622C.

FIG. 6D is a simplified schematic diagram illustrating still another embodiment of a portion of the catheter system 600D that generates the pre-bubble 644D. In this embodiment, the catheter system 600D includes a catheter shaft 610D, a light guide 622D and a pre-bubble generator 654D. The pre-bubble generator 654D generates the pre-bubble 644D to provide a gap between the light guide 622D and a plasma pulse (not shown in FIG. 6D) that will ultimately be generated. In one such embodiment, the pre-bubble generator 654D can include a hydrophobic coating. Alternatively, or in addition, the pre-bubble generator 654D can include a nano-textured surface or any other surface or material that would encourage or promote generation of a pre-bubble at or near a distal end 660D of the light guide 622D. In this embodiment, the pre-bubble generator 654D is positioned on the light guide 622D. However, it is recognized that the pre-bubble generator 654D can be positioned at or on another structure within the catheter system 600D. With this design, damage to the light guide 622D is inhibited because the plasma pulse does not occur immediately at or on the light guide 622D, but instead occurs away from the light guide 622D.

Light Guides

The light guides illustrated and/or described herein can include an optical fiber or flexible light pipe. The light guides illustrated and/or described herein can be thin and flexible and can allow light signals to be sent with very little loss of strength. The light guides illustrated and/or described herein can include a core surrounded by a cladding about its circumference. In some embodiments, the core can be a cylindrical core or a partially cylindrical core. The core and cladding of the light guides can be formed from one or more materials, including but not limited to one or more types of glass, silica, or one or more polymers. The light guides may also include a protective coating, such as a polymer. It is appreciated that the index of refraction of the core will be greater than the index of refraction of the cladding.

Each light guide can guide light along its length to a distal portion having at least one optical window. The light guides can create a light path as portion of an optical network including a power source. The light path within the optical network allows light to travel from one part of the network to another. Either or both of the optical fiber or the flexible light pipe can provide a light path within the optical networks herein.

The light guides illustrated and/or described herein can assume many configurations about the catheter shaft of the catheters illustrated and/or described herein. In some embodiments, the light guides can run parallel to the longitudinal axis of the catheter shaft of the catheter. In some embodiments, the light guides can be disposed spirally or helically about the longitudinal axis of the catheter shaft of the catheter. In some embodiments, the light guides can be physically coupled to the catheter shaft. In other embodiments, the light guides can be disposed along the length of the outer diameter of the catheter shaft. In yet other embodiments the light guides herein can be disposed within one or more light guide lumens within the catheter shaft. Various configurations for the catheter shafts and light guide lumens will be discussed below.

Power Sources

The power sources suitable for use herein can include various types of power sources including lasers and lamps. Suitable lasers can include short pulse lasers on the sub-millisecond timescale. In some embodiments, the power source can include lasers on the nanosecond (ns) timescale. The lasers can also include short pulse lasers on the picosecond (ps), femtosecond (fs), and microsecond (us) timescales. It is appreciated that there are many combinations of laser wavelengths, pulse widths and energy levels that can be employed to achieve plasma in the balloon fluid of the catheters illustrated and/or described herein. In various embodiments, the pulse widths can include those falling within a range including from at least 10 ns to 200 ns. In some embodiments, the pulse widths can include those falling within a range including from at least 20 ns to 100 ns. In other embodiments, the pulse widths can include those falling within a range including from at least 1 ns to 5000 ns.

Exemplary nanosecond lasers can include those within the UV to IR spectrum, spanning wavelengths of about 10 nanometers to 1 millimeter. In some embodiments, the power sources suitable for use in the catheter systems herein can include those capable of producing light at wavelengths of from at least 750 nm to 2000 nm. In some embodiments, the power sources can include those capable of producing light at wavelengths of from at least 700 nm to 3000 nm. In some embodiments, the power sources can include those capable of producing light at wavelengths of from at least 100 nm to 10 micrometers (μm). Nanosecond lasers can include those having repetition rates of up to 200 kHz. In some embodiments, the laser can include a Q-switched thulium:yttrium-aluminum-garnet (Tm:YAG) laser. In some embodiments, the laser can include a neodymium:yttrium-aluminum-garnet (Nd:YAG), holmium:yttrium-aluminum-garnet (Ho:YAG), erbium:yttrium-aluminum-garnet (Er:YAG), excimer laser, helium-neon laser, carbon dioxide laser, as well as doped, pulsed, fiber lasers.

Pressure Waves

The catheters illustrated and/or described herein can generate pressure waves having maximum pressures in the range of at least 1 megapascal (MPa) to 100 MPa. The maximum pressure generated by a particular catheter will depend on the power source, the absorbing material, the bubble expansion, the propagation medium, the balloon material, and other factors. In some embodiments, the catheters illustrated and/or described herein can generate pressure waves having maximum pressures in the range of at least 2 MPa to 50 MPa. In other embodiments, the catheters illustrated and/or described herein can generate pressure waves having maximum pressures in the range of at least 2 MPa to 30 MPa. In yet other embodiments, the catheters illustrated and/or described herein can generate pressure waves having maximum pressures in the range of at least 15 MPa to 25 MPa. In some embodiments, the catheters illustrated and/or described herein can generate pressure waves having peak pressures of greater than or equal to 1 MPa, 2 MPa, 3 MPa, 4 MPa, 5 MPa, 6 MPa, 7 MPa, 8 MPa, 9 MPa, 10 MPa, 11 MPa, 12 MPa, 13 MPa, 14 MPa, 15 MPa, 16 MPa, 17 MPa, 18 MPa, 19 MPa, 20 MPa, 21 MPa, 22 MPa, 23 MPa, 24 MPa, 25 MPa, 26 MPa, 27 MPa, 28 MPa, 29 MPa, 30 MPa, 31 MPa, 32 MPa, 33 MPa, 34 MPa, 35 MPa, 36 MPa, 37 MPa, 38 MPa, 39 MPa, 40 MPa, 41 MPa, 42 MPa, 43 MPa, 44 MPa, 45 MPa, 46 MPa, 47 MPa, 48 MPa, 49 MPa, or 50 MPa. It is appreciated that the catheters illustrated and/or described herein can generate pressure waves having operating pressures or maximum pressures that can fall within a range, wherein any of the forgoing numbers can serve as the lower or upper bound of the range, provided that the lower bound of the range is a value less than the upper bound of the range.

Therapeutic treatment can act via a fatigue mechanism or a brute force mechanism. For a fatigue mechanism, operating pressures would be about at least 0.5 MPa to 2 MPa, or about 1 MPa. For a brute force mechanism, operating pressures would be about at least 20 MPa to 30 MPa, or about 25 MPa. Pressures between the extreme ends of these two ranges may act upon a treatment site using a combination of a fatigue mechanism and a brute force mechanism.

The pressure waves described herein can be imparted upon the treatment site from a distance within a range from at least 0.1 millimeters (mm) to 25 mm extending radially from a longitudinal axis of a catheter placed at a treatment site. In some embodiments, the pressure waves can be imparted upon the treatment site from a distance within a range from at least 10 mm to 20 mm extending radially from a longitudinal axis of a catheter placed at a treatment site. In other embodiments, the pressure waves can be imparted upon the treatment site from a distance within a range from at least 1 mm to 10 mm extending radially from a longitudinal axis of a catheter placed at a treatment site. In yet other embodiments, the pressure waves can be imparted upon the treatment site from a distance within a range from at least 1.5 mm to 4 mm extending radially from a longitudinal axis of a catheter placed at a treatment site. In some embodiments, the pressure waves can be imparted upon the treatment site from a range of at least 2 MPa to 30 MPa at a distance from 0.1 mm to 10 mm. In some embodiments, the pressure waves can be imparted upon the treatment site from a range of at least 2 MPa to 25 MPa at a distance from 0.1 mm to 10 mm. In some embodiments, the pressure waves can be imparted upon the treatment site from a distance that can be greater than or equal to 0.1 mm, 0.2 mm, 0.3 mm, 0.4 mm, 0.5 mm, 0.6 mm, 0.7 mm, 0.8 mm, 0.9 mm, 1 mm, 2 mm, 3 mm, 4 mm, 5 mm, 6 mm, 7 mm, 8 mm, 9 mm, or 10 mm, or can be an amount falling within a range between any of the foregoing.

It should be noted that, as used in this specification and the appended claims, the singular forms "a," "an," and "the" include plural referents unless the content and/or context clearly dictates otherwise. It should also be noted that the term "or" is generally employed in its sense including "and/or" unless the content or context clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

As used herein, the recitation of numerical ranges by endpoints shall include all numbers subsumed within that range, inclusive (e.g., 2 to 8 includes 2, 2.1, 2.8, 5.3, 7, 8, etc.).

It is recognized that the figures shown and described are not necessarily drawn to scale, and that they are provided for ease of reference and understanding, and for relative positioning of the structures.

The headings used herein are provided for consistency with suggestions under 37 CFR 1.77 or otherwise to provide organizational cues. These headings shall not be viewed to limit or characterize the invention(s) set out in any claims that may issue from this disclosure. As an example, a description of a technology in the "Background" is not an admission that technology is prior art to any invention(s) in this disclosure. Neither is the "Summary" or "Abstract" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

It is understood that although a number of different embodiments of the catheter systems have been illustrated and described herein, one or more features of any one embodiment can be combined with one or more features of one or more of the other embodiments, provided that such combination satisfies the intent of the present invention.

While a number of exemplary aspects and embodiments of the catheter systems have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope, and no limitations are intended to the details of construction or design herein shown.

What is claimed is:

1. A catheter system for treating a treatment site within or adjacent to a vessel wall or heart valve, the catheter system comprising:

a power source that generates a plurality of energy pulses;

a controller that controls the power source so that the plurality of energy pulses cooperate to produce a composite energy pulse having a composite pulse shape;

a light guide that receives the composite energy pulse, the light guide emitting light energy in a direction away from the light guide to generate a plasma pulse away from the light guide; and an inflatable balloon that encircles a distal end of the light guide, the composite energy pulse generating a plurality of plasma pulses away from the distal end of the light guide, wherein the catheter system is configured to generate a pre-bubble at the distal end of the light guide so that the plasma pulse is generated away from the light guide.

2. The catheter system of claim 1 wherein the power source is a laser.

3. The catheter system of claim 1 wherein the light guide is an optical fiber.

4. The catheter system of claim 1 wherein each of the plurality of energy pulses are sub-millisecond pulses.

5. The catheter system of claim 1 wherein the composite energy pulse is configured to generate the pre-bubble at the distal end of the light guide.

6. The catheter system of claim 1 wherein the pre-bubble is generated by electrolysis.

7. The catheter system of claim 1 wherein the pre-bubble is generated by using a resistive heater.

8. The catheter system of claim 1 further comprising a nano surface that is positioned near the distal end of the light guide.

9. The catheter system of claim 1 further comprising a nano surface that is positioned on the distal end of the light guide.

10. The catheter system of claim 9 wherein the nano surface is textured.

11. The catheter system of claim 1 further comprising a hydrophobic material that is positioned on the distal end of the light guide.

12. The catheter system of claim 1 further comprising a hydrophobic material that is positioned near the distal end of the light guide.

13. The catheter system of claim 1 wherein each of the energy pulses has a pulse width, and the energy pulses are added to one another so that the composite energy pulse has a pulse width that is longer than the pulse width of any one of the energy pulses.

14. The catheter system of claim 1 wherein the composite energy pulse has a pulse amplitude that increases over time.

15. The catheter system of claim 1 wherein the composite energy pulse has a pulse amplitude that decreases over time.

16. The catheter system of claim 1 wherein the plurality of plasma pulses are generated at different times from one another.

17. The catheter system of claim 1 wherein the controller controls a timing of the composite energy pulse relative to a start of the generation of the pre-bubble.

18. The catheter system of claim 17 wherein the composite energy pulse is generated greater than approximately 1 ns and less than approximately 100 ms after the start of the generation of the pre-bubble.

19. A catheter system for treating a treatment site within or adjacent to a vessel wall or heart valve, the catheter system comprising:

a power source that generates a plurality of energy pulses, the power source including a laser;

a controller that controls the power source so that the plurality of energy pulses overlap and combine to produce a composite energy pulse having a composite pulse shape;

a light guide that receives the composite energy pulse, the light guide emitting light energy in a direction away from the light guide to generate a plasma pulse away from the light guide, the light guide including an optical fiber; and an inflatable balloon that encircles a distal end of the light guide, wherein the catheter system is configured to generate a pre-bubble at the distal end of the light guide so that the plasma pulse is generated away from the light guide.

20. A catheter system for treating a treatment site within or adjacent to a vessel wall or heart valve, the catheter system comprising:

a power source that generates a plurality of energy pulses;

a controller that controls the power source so that the plurality of energy pulses overlap and combine to produce a composite energy pulse having a composite pulse shape;

a light guide that receives the composite energy pulse, the light guide emitting light energy in a direction away from the light guide to generate a plasma pulse away from the light guide;

an inflatable balloon that encircles a distal end of the light guide; and a nano surface that is positioned near the distal end of the light guide, wherein the catheter system is configured to generate a pre-bubble at the distal end of the light guide so that the plasma pulse is generated away from the light guide.

* * * * *